(12) United States Patent
Xiao et al.

(10) Patent No.: US 10,683,507 B2
(45) Date of Patent: Jun. 16, 2020

(54) MATERIALS AND METHODS FOR RAPID AND SPECIFIC DETECTION OF SYNTHETIC CATHINONES

(71) Applicants: Yi Xiao, Miami, FL (US); Haixiang Yu, Miami, FL (US)

(72) Inventors: Yi Xiao, Miami, FL (US); Haixiang Yu, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/900,061

(22) Filed: Feb. 20, 2018

(65) Prior Publication Data

US 2019/0256852 A1    Aug. 22, 2019

(51) Int. Cl.
| | |
|---|---|
| *C12N 15/11* | (2006.01) |
| *C12N 15/115* | (2010.01) |
| *C09B 23/01* | (2006.01) |
| *C07C 225/10* | (2006.01) |
| *G01N 33/50* | (2006.01) |

(52) U.S. Cl.
CPC .......... *C12N 15/115* (2013.01); *C07C 225/10* (2013.01); *C09B 23/0066* (2013.01); *G01N 33/50* (2013.01); *C12N 2310/16* (2013.01); *C12N 2310/3517* (2013.01); *C12N 2320/13* (2013.01)

(58) Field of Classification Search
CPC .............. C12N 15/115; C12N 15/1048; C12N 2310/16
See application file for complete search history.

(56) References Cited

U.S. PATENT DOCUMENTS

| | | | | |
|---|---|---|---|---|
| 2013/0210167 A1* | 8/2013 | Benchikh | ............. | C07D 405/06 436/501 |
| 2014/0187437 A1* | 7/2014 | Stojanovic | ............. | B60G 15/12 506/9 |

OTHER PUBLICATIONS

Mao et al., G-quadruplex-heroin DNAzyme molecular beacon probe for the detection of methamphetamine, Royal Society of Chemistry Advances, vol. 6, pp. 62754-62759. (Year: 2016).*

(Continued)

*Primary Examiner* — Dana H Shin
(74) *Attorney, Agent, or Firm* — Saliwanchik, Lloyd & Eisenschenk

(57) ABSTRACT

The subject invention provides methods, assays, and products for detecting small molecules in a sample, in particular, in both clinical and field settings. The method for detecting a small-molecule target, preferably, a synthetic cathinone in a sample comprises contacting the sample with an aptamer-based sensor selective for the small-molecule target, and detecting the small-molecule target in the sample. Specifically, the method utilizes an aptamer-based sensor comprising a dye binding to a three-way junction binding domain of an aptamer. Binding of small-molecule target to the aptamer displaces the dye, generating a spectroscopic signal that can be used for detection of the small-molecule target and quantitative measurement of the target concentration.

18 Claims, 8 Drawing Sheets

Specification includes a Sequence Listing.

(56) References Cited

OTHER PUBLICATIONS

Choi, J. K. et al., "3,3'-Diethylthiatricarbocyanine Iodide: A Highly Sensitive Chiroptical Reporter of DNA Helicity and Sequence." Int. J. Mol. Sci., 2011, 12: 8052-8062.

Crooks, G. E. et al., "WebLogo: A Sequence Logo Generator." Genome Research, Mar. 2018, 14: 1188-1190.

Garoff, R. A. et al., "Helical Aggregation of Cyanine Dyes on DNA Templates: Effect of Dye Structure on Formation of Homo- and Heteroaggregates." Langmuir, Mar. 2002, 18: 6330-6337.

Iliuk, A. B. et al., "Aptamer in Bioanalytical Applications." Anal. Chem., 2011, 83: 4440-4452.

Neves, M. A. D. et al., "Defining the secondary structural requirements of a cocaine-binding aptamer by a thermodynamic and mutation study." Ciophysical Chemistry, 2010, 153: 9-16.

Nutiu, R., Li, Y., "In Vitro Selection of Structure-Switching Signaling Aptamers." Angew. Chem. Int. Ed., 2005, 44: 1061-1065.

Nutiu, R. Li, Y., "Structure-Switching Signaling Aptamers." J. Am. Chem. Soc., 2003, 125: 4771-4778.

Oh, S. S. et al., "In Vitro Selection of Shape-Changing DNA Nanostructures Capable of Binding-Induced Cargo Release." ACSNano, 2013, 7 (11): 9675-9683.

Rajendran, M., Ellington, A. D., "In Vitro Selection of Molecular Beacons." Nucleic Acids Research, 2003, 31 (19): 5700-5713.

Roncancio, D. et al., "A Label-Free Aptamer-Fluorophore Assembly for Rapid and Specific Detection of Cocaine in Biofluids." Analytical Chemistry, 2014, 86: 11100-11106.

Seifert, J. L. et al., "Spontaneous Assembly of Helical Cyanine Dye Aggregates on DNA Nanotemplates." J. Am. Chem. Soc., 1999, 121: 2987-2995.

Song, S. et al., "Aptamer-based biosensors." Trends in Analytical Chemistry, 2008, 27 (2): 108-117.

Stojanovic, M. N., Landry, D. W., "Aptamer-based Colorimetric Probe for Cocaine." J. Am. Chem. Soc., 2002, 124: 9678-9679.

Stojanovic, M. N., et al., "Aptamer-Based Folding Fluorescent Sensor for Cocaine." J. Am. Chem. Soc., 2001, 123: 4928-4931.

Stojanovic, M. N. et al., "Fluorescent Sensors Based on Aptamer Self-Assembly." J. Am. Chem. Soc., 2000, 122: 11547-11548.

Tuerck, C., Gold, L., "Systematic Evolution of Ligands by Exponential Enrichment: RNA Ligans to Bacteriophage T4 DNA Polymerase." Science, Aug. 1990, 249 (4968): 505-510.

Yang, K. et al., "Optimizing Cross-reactivity with Evolutionary Search for Sensors." J. Am. Chem. Soc., 2012, 134: 1642-1647.

Yang, K. et al., "Recognition and sensing of low-epitope targets via ternary complexes with oligonucleotides and synthetic receptors." Nature Chemistry, Nov. 2014, 6: 1003-1008.

Zangi, R. et al., "Effect of Ions on the Hydrophobic Interaction between Two Plates." J. Am. Chem. Soc., 2007, 129: 4678-4686.

\* cited by examiner

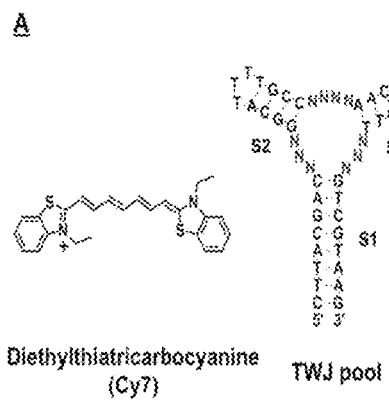
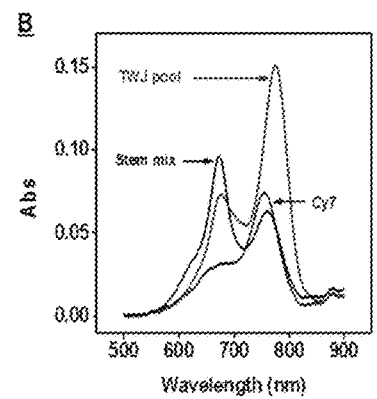
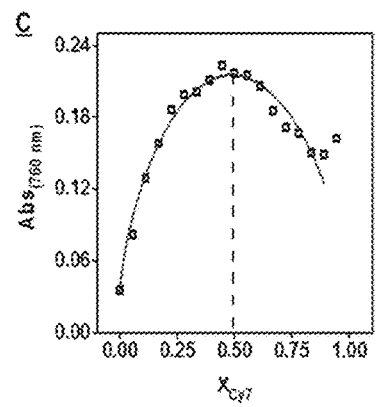
FIG. 1A  FIG. 1B  FIG. 1C
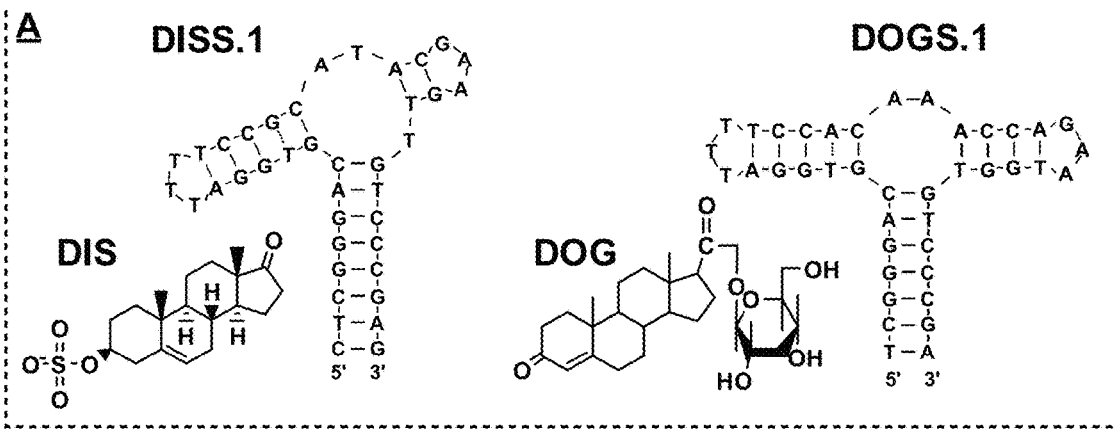
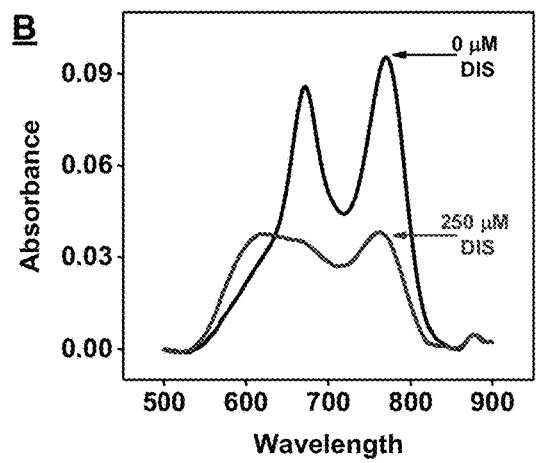
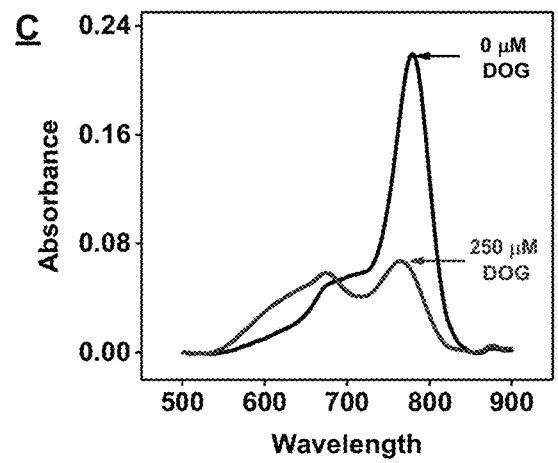
FIG. 2B  FIG. 2C

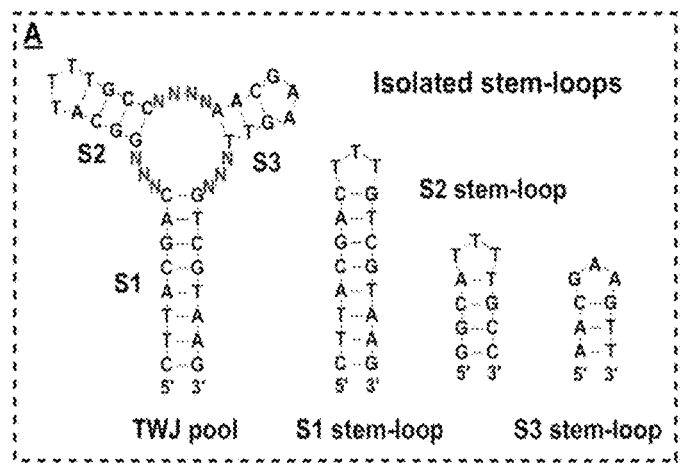
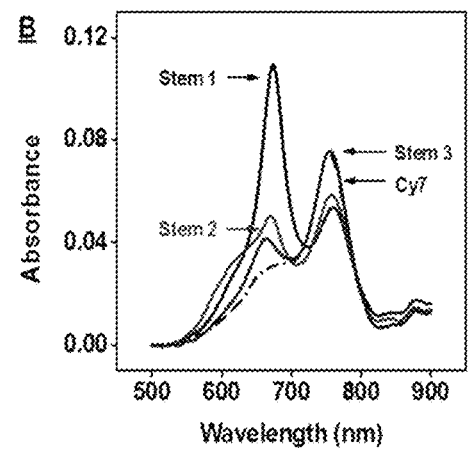
FIG. 3A
FIG. 3B
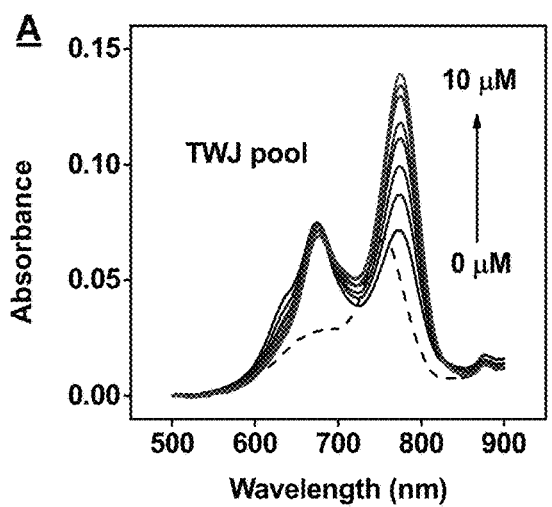
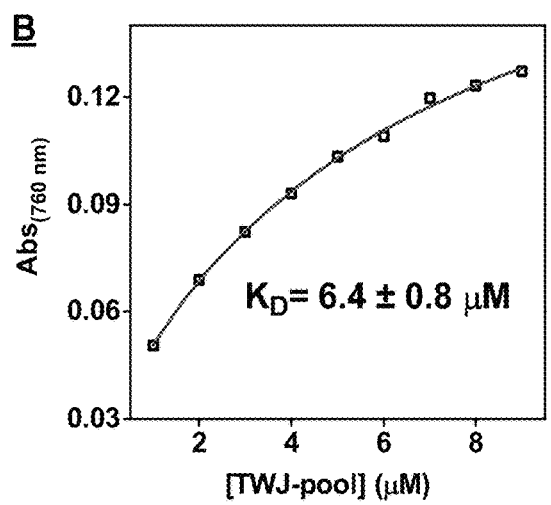
FIG. 4A
FIG. 4B

FIG. 9A
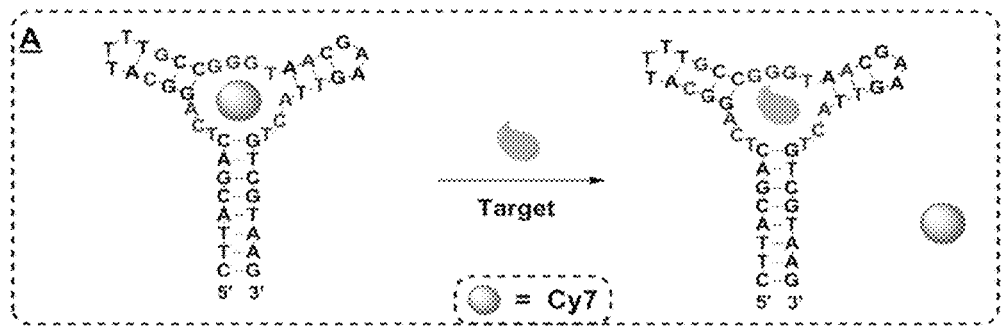
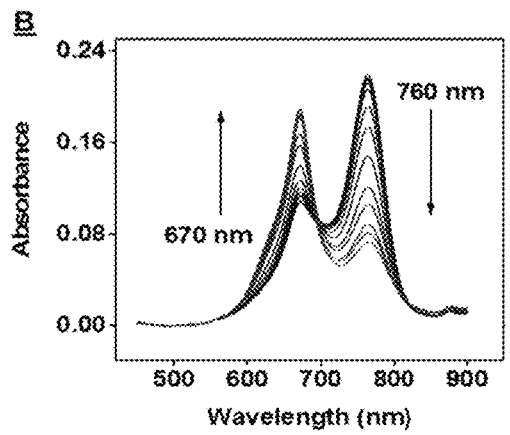
FIG. 9B
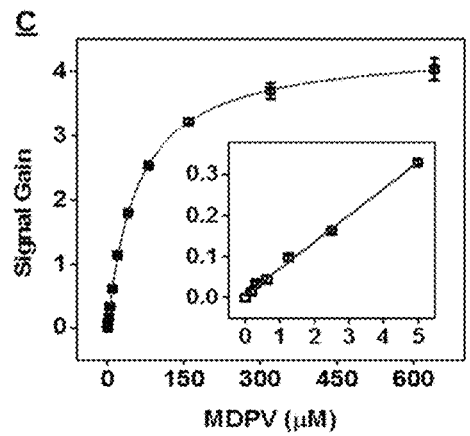
FIG. 9C
FIG. 10A
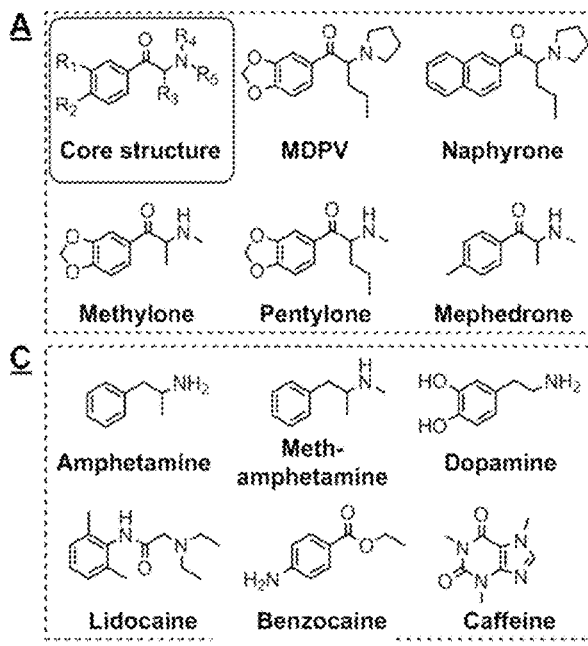
FIG. 10C
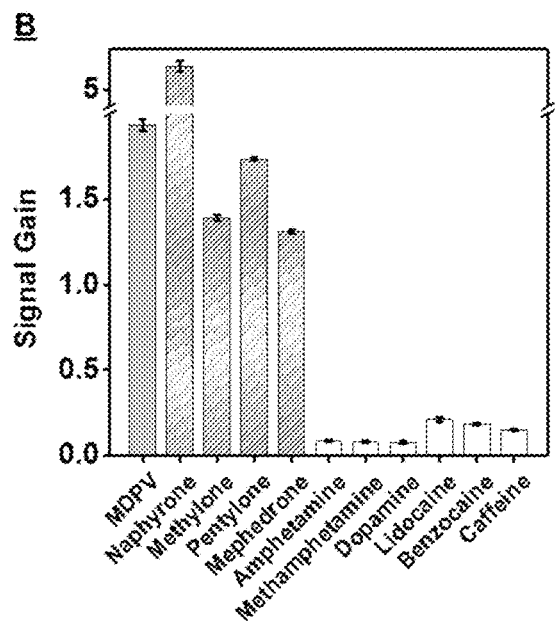
FIG. 10B

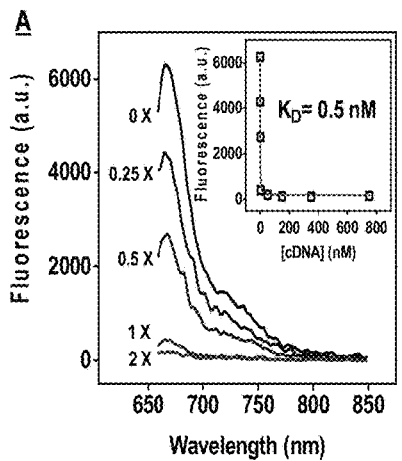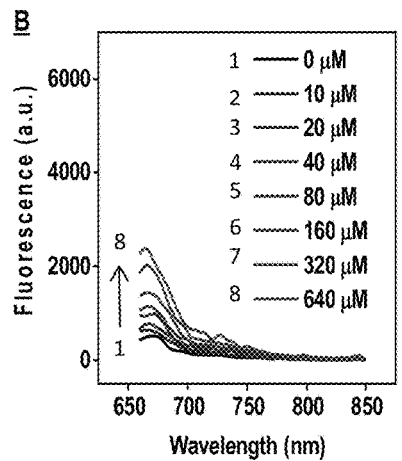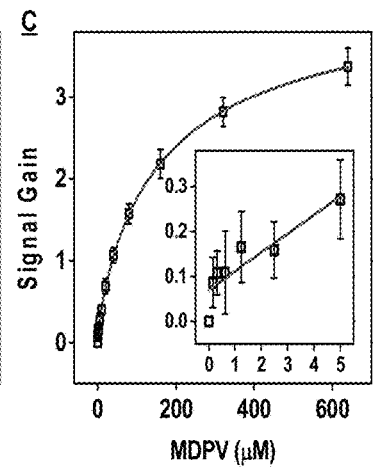
FIG. 13A  FIG. 13B  FIG. 13C
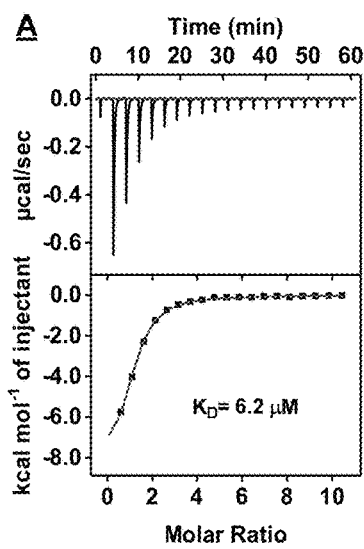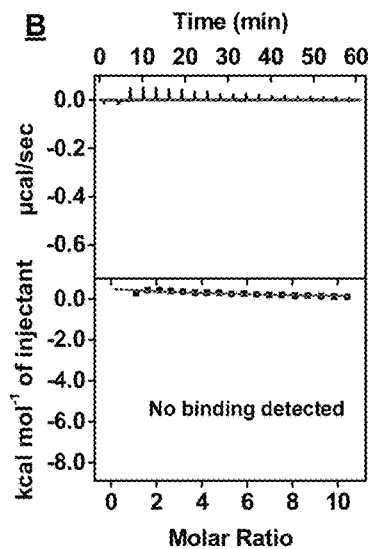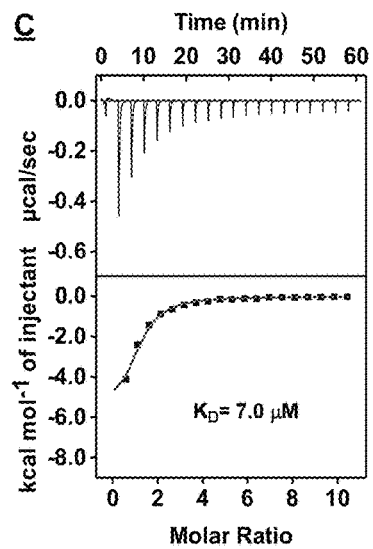
FIG. 14A  FIG. 14B  FIG. 14C

SEQUENCE LISTING

```
<160> NUMBER OF SEQ ID NOS: 17

<210> SEQ ID NO 1
<211> LENGTH: 39
<212> TYPE: DNA
<213> ORGANISM: Artificial
<220> FEATURE:
<223> OTHER INFORMATION: aptamer

<400> SEQUENCE: 1
ctcgggacgt ggattttccg catacgaagt tgtcccgag                     39

<210> SEQ ID NO 2
<211> LENGTH: 40
<212> TYPE: DNA
<213> ORGANISM: Artificial
<220> FEATURE:
<223> OTHER INFORMATION: aptamer

<400> SEQUENCE: 2
tcgggacgtg gattttccac aaaccagaat ggtgtcccga                    40

<210> SEQ ID NO 3
<211> LENGTH: 46
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (23)..(26)
<223> OTHER INFORMATION: n is a, c, g, or t
<220> FEATURE:
<221> NAME/KEY: misc_feature
<222> LOCATION: (36)..(38)
<223> OTHER INFORMATION: n is a, c, g, or t
```

-continued

<400> SEQUENCE: 3
cttacgacnn nggcattttg ccnnnnaacg aagttnnngt cgtaag      46

<210> SEQ ID NO 4
<211> LENGTH: 73
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (24)..(26)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(41)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(53)
<223> OTHER INFORMATION: n is a, c, g, or t

<400> SEQUENCE: 4
cgagcatagg cagaacttac gacnnnggna ttttnccnnn nancgaagnt nnngtcgtaa      60
gagcgagtca ttc      73

<210> SEQ ID NO 5
<211> LENGTH: 19
<212> TYPE: DNA
<213> ORGANISM: Artificial
<220> FEATURE:
<223> OTHER INFORMATION: aptamer

<400> SEQUENCE: 5
cttacgactt tgtcgtaag      19

<210> SEQ ID NO 6
<211> LENGTH: 11
<212> TYPE: DNA
<213> ORGANISM: Artificial
<220> FEATURE:
<223> OTHER INFORMATION: aptamer

<400> SEQUENCE: 6
ggcattttgc c      11

<210> SEQ ID NO 7
<211> LENGTH: 9
<212> TYPE: DNA
<213> ORGANISM: Artificial
<220> FEATURE:
<223> OTHER INFORMATION: aptamer

```
<400> SEQUENCE: 7 aacgaagtt                                                                    9

<210> SEQ ID NO 8
<211> LENGTH: 25
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (25)..(25)
<223> OTHER INFORMATION: biotin modification

<400> SEQUENCE: 8
tttttgtcgt aagttctgcc atttt                                                 25

<210> SEQ ID NO 9
<211> LENGTH: 20
<212> TYPE: DNA
<213> ORGANISM: Artificial
<220> FEATURE:
<223> OTHER INFORMATION: aptamer

<400> SEQUENCE: 9
gcagcatagg cagaacttac                                                       20

<210> SEQ ID NO 10
<211> LENGTH: 20
<212> TYPE: DNA
<213> ORGANISM: Artificial
<220> FEATURE:
<223> OTHER INFORMATION: aptamer

<400> SEQUENCE: 10
gaatgactcg ctcttacgac                                                       20

<210> SEQ ID NO 11
<211> LENGTH: 20
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(1)
<223> OTHER INFORMATION: biotin modification

<400> SEQUENCE: 11
gaatgactcg ctcttacgac                                                       20

<210> SEQ ID NO 12
<211> LENGTH: 46
<212> TYPE: DNA
<213> ORGANISM: Artificial
<220> FEATURE:
<223> OTHER INFORMATION: aptamer

<400> SEQUENCE: 12
cttacgactc aggcattttg ccgggtaacg aagttactgt cgtaag                          46

<210> SEQ ID NO 13
<211> LENGTH: 51
<212> TYPE: DNA
<213> ORGANISM: Artificial
<220> FEATURE:
<223> OTHER INFORMATION: aptamer
```

```
<400> SEQUENCE: 13
cagaacttac gactcaggca ttttgccggg taacgaagtt actgtcgtaa g            51

<210> SEQ ID NO 14
<211> LENGTH: 53
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (1)..(1)
<223> OTHER INFORMATION: Cy5 fluorophore modification

<400> SEQUENCE: 14
ggcagaactt acgactcagg cattttgccg ggtaacgaag ttactgtcgt aag          53

<210> SEQ ID NO 15
<211> LENGTH: 15
<212> TYPE: DNA
<213> ORGANISM: Artificial
<220> FEATURE:
<223> OTHER INFORMATION: aptamer

<400> SEQUENCE: 15
gtcgtaagtt ctgcc                                                    15

<210> SEQ ID NO 16
<211> LENGTH: 15
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (15)..(15)
<223> OTHER INFORMATION: Iowa Black RQ quencher modification

<400> SEQUENCE: 16
gtcgtaagtt ctgcc                                                    15

<210> SEQ ID NO 17
<211> LENGTH: 46
<212> TYPE: DNA
<213> ORGANISM: Artificial
<220> FEATURE:
<223> OTHER INFORMATION: aptamer
<220> FEATURE:
<221> NAME/KEY: misc_feature
<222> LOCATION: (9)..(9)
<223> OTHER INFORMATION: n is t, c, or a
<220> FEATURE:
<221> NAME/KEY: misc_feature
<222> LOCATION: (10)..(10)
<223> OTHER INFORMATION: n is c, g, a, or t
<220> FEATURE:
<221> NAME/KEY: misc_feature
<222> LOCATION: (11)..(11)
<223> OTHER INFORMATION: n is a, t, or c
<220> FEATURE:
<221> NAME/KEY: misc_feature
<222> LOCATION: (14)..(14)
<223> OTHER INFORMATION: n is c or g
<220> FEATURE:
<221> NAME/KEY: misc_feature
<222> LOCATION: (17)..(18)
<223> OTHER INFORMATION: n is t or c
<220> FEATURE:
<221> NAME/KEY: misc_feature
<222> LOCATION: (20)..(20)
```

```
<223> OTHER INFORMATION: n is g, c, or t
<220> FEATURE:
<221> NAME/KEY: misc_feature
<222> LOCATION: (23)..(23)
<223> OTHER INFORMATION: n is g, a, c, or t
<220> FEATURE:
<221> NAME/KEY: misc_feature
<222> LOCATION: (24)..(24)
<223> OTHER INFORMATION: n is g, t, c, or a
<220> FEATURE:
<221> NAME/KEY: misc_feature
<222> LOCATION: (25)..(25)
<223> OTHER INFORMATION: n is g, t, or c
<220> FEATURE:
<221> NAME/KEY: misc_feature
<222> LOCATION: (26)..(26)
<223> OTHER INFORMATION: n is t, c, or a
<220> FEATURE:
<221> NAME/KEY: misc_feature
<222> LOCATION: (28)..(28)
<223> OTHER INFORMATION: n is a, g, or t
<220> FEATURE:
<221> NAME/KEY: misc_feature
<222> LOCATION: (31)..(31)
<223> OTHER INFORMATION: n is a, g, or t
<220> FEATURE:
<221> NAME/KEY: misc_feature
<222> LOCATION: (34)..(34)
<223> OTHER INFORMATION: n is t, a, or c
<220> FEATURE:
<221> NAME/KEY: misc_feature
<222> LOCATION: (35)..(35)
<223> OTHER INFORMATION: n is t or g
<220> FEATURE:
<221> NAME/KEY: misc_feature
<222> LOCATION: (37)..(37)
<223> OTHER INFORMATION: n is c or g
<220> FEATURE:
<221> NAME/KEY: misc_feature
<222> LOCATION: (38)..(38)
<223> OTHER INFORMATION: n is t or g
<220> FEATURE:
<221> NAME/KEY: misc_feature
<222> LOCATION: (41)..(41)
<223> OTHER INFORMATION: n is c or a

<400> SEQUENCE: 17
cttacgacnn nggnatnntn ccnnnnancg nagnnanngt ngtaag                46
```

MATERIALS AND METHODS FOR RAPID AND SPECIFIC DETECTION OF SYNTHETIC CATHINONES

GOVERNMENT SUPPORT

The invention was made with government support under DA036821 awarded by National Institutes of Health, and 2015-R2-CX-0034 awarded by National Institute of Justice. The government has certain rights in the invention.

SEQUENCE LISTING

The Sequence Listing for this application is labeled "SeqList-27Jun19-ST25.txt," which was created on Jun. 27, 2019, and is 6 KB. The Sequence Listing is incorporated herein by reference in its entirety.

BACKGROUND

The biosensor field is on a continuous quest for ever-greater sensitivity. In conventional bioassays, where the signal is directly proportional to the target concentration, the sensitivity is determined by the intrinsic target affinity of the bioreceptor being used for detection. In this scenario, it would be difficult to generate a measurable signal at target concentrations more than 100-fold lower than the dissociation constant ($K_D$) of the bioreceptor.

Small molecules are important targets with the potential of clinical or commercial applications. Thus, efforts to develop methods for portable, low-cost and quantitative detection of a broad range of small molecules on site are gaining momentum. Methods that are highly sensitive and selective, including high-performance liquid chromatography (HPLC), gas chromatography-mass spectrometry (GC-MS), fluorescence and electrochemistry, have been used for the detection of small molecules. However, these methods are time-consuming and require expensive reagents, advanced equipment, complex sample preparation, and trained operators. As a result, colorimetric methods have attracted interest for on-site and real-time detection of small molecules, due to their unique properties including cost-efficiency, lack of instrumentation, rapidness, and simplicity.

Aptamers are nucleic acid-based molecules that can be isolated in vitro through systematic evolution of ligands by exponential enrichment (SELEX) processes to bind various targets with high specificity and affinity,[1] including proteins, metal ions, small molecules, and even whole cells. They are increasingly being used as recognition elements in biosensing platforms due to their low cost of production, ease of modification, chemical stability, and long shelf life.[2,3] The generation of a sensor readout typically requires an aptamer to undergo some manner of binding-induced change, and most aptamer-based sensors utilize structure-switching aptamers that undergo a major conformational rearrangement upon target binding. However, most aptamers do not innately undergo a measureable binding-induced conformational change, and the development of a structure-switching aptamer typically entails a multi-stage process of sequence analysis and chemical modification.

After identifying the target-binding domain of a newly-isolated aptamer through truncation,[4] structure-switching functionality is then introduced via methods such as sequence engineering,[4] splitting,[5] or utilization of a complementary strand.[6] These methods are laborious and require considerable trial and error. Additionally, engineered structure-switching aptamers often have low target-binding affinities, which limit their utility.

SELEX methods have been developed that make it possible to isolate aptamers with inherent structure-switching functionality. For example, Ellington[7] and Li[8] utilized a 'strand-displacement' strategy to directly isolate structure-switching aptamers. Their approach begins with the hybridization of library molecules with an immobilized complementary strand. Library strands that bind to the target undergo a conformational change, dissociate from the complementary strand, and are collected in the supernatant. After several rounds of isolation and enrichment, these aptamers are sequenced, chemically modified with a fluorophore, and can then be directly employed in strand-displacement assays with a quencher-modified complementary strand.

This approach eliminates the need for sequence engineering, but there is an inherent conflict between the requirements for aptamer isolation and sensor development. This is because the isolation of high-affinity aptamers requires strong hybridization of the complementary strand with the library molecules in order to create an energetic barrier for stringent selection. However, since the complementary strands have high binding affinity for the aptamer, they inadvertently inhibit target-binding and consequently reduce the sensitivity of strand-displacement assays. This is particularly problematic for the detection of small-molecule targets, which usually have low affinity for aptamers. As such, the limit of detection of strand-displacement assays for small molecules is usually comparable to or even higher than the dissociation constant of the employed aptamer. Moreover, such assays require a heating-and-cooling process lasting ≥30 min to ensure complete hybridization between the complementary strand and aptamer to achieve low background. This time-consuming step greatly hinders the use of these assays for rapid on-site detection. Nonetheless, the strand-displacement assay is presently the only generally applicable method for developing aptamer-based small-molecule sensors directly from isolated aptamers without further engineering.

Synthetic cathinones (also known as 'bath salts') are designer drugs sharing a similar core structure with amphetamines and 3,4-methylenedioxy-methamphetamine (MDMA). They are highly addictive central nervous system stimulants, and are associated with many negative health consequences, including even death. Although these drugs have emerged only recently, abuse of bath salts has become a threat to public health and safety due to their severe toxicity, increasingly broad availability, and difficulty of regulation. More importantly, there is currently no reliable presumptive test for any synthetic cathinone. Chemical spot tests used to detect conventional drugs such as cocaine, methamphetamine, and opioids show no cross-reactivity to synthetic cathinones.

Therefore, there is a need for methods and materials to rapidly and selectively detect small molecules such as synthetic cathinones, in particular, for clinical or field setting.

BRIEF SUMMARY

The subject invention provides methods, assays, and products for detecting small molecules in a complex sample, in particular, in both clinical and field settings. In one embodiment, the method comprises providing a sample, contacting the sample with an aptamer-based sensor selective for the small-molecule target, and detecting the small-molecule target in the sample. Preferably, the aptamer-based sensor is a DNA aptamer selective for the small-molecule target.

In one embodiment, the sample is a biological sample of a subject. In specific embodiments, the biological sample is selected from blood, plasma, urine, tears, and saliva. The subject may be any animal or human, preferably, a human. The subject may also be any animal including, but not limited to, non-human primates, rodents, dogs, cats, horses, cattle, pigs, sheep, goats, chickens, guinea pigs, hamsters and the like.

In one embodiment, the sample is an environmental sample, for example, water, soil, air, or plant sample.

In one embodiment, the detection of the small-molecule target comprises measuring a signal generated upon assembly of the aptamer-target complex. In another embodiment, the method further comprises determining the concentration of the small-molecule target in the sample.

In another embodiment, the small molecule is a drug molecule such as a cathinone, a cathinone derivative, or synthetic cathinone, such as ring-substituted cathinone derivative.

In one embodiment, the synthetic cathinone may have a core structure of formula (I)

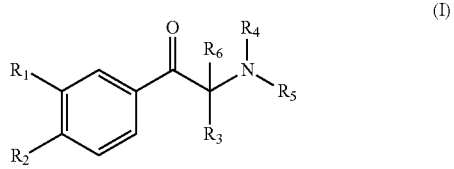

wherein $R_1$, $R_2$, $R_3$, $R_4$, $R_5$, and $R_6$ are each independently selected from the group consisting of hydrogen, alkyl, substituted alkyl, aryl, substituted aryl, benzyl, heteroaryl, substituted heteroaryl, cycloalkyl, substituted cycloalkyl, cycloalkenyl, substituted cycloalkenyl, heterocycloalkyl, alkenyl, alkynyl, alkoxy, thiol, haloalkyl, acyl, halogen, amino, alkylamino, hydroxyl, hydroxylalkyl, and —COOH.

In one embodiment, $R_1$ and $R_2$, are each independently selected from the group consisting of hydrogen, alkyl, aryl, heteroaryl, cycloalkyl, cycloalkenyl, heterocycloalkyl, alkenyl, alkynyl, haloalkyl, acyl, alkoxy, halogen, and hydroxylalkyl; $R_3$ is hydrogen or alkyl. $R_4$ and $R_5$ are each independently selected from the group consisting of hydrogen, alkyl, aryl, heteroaryl, cycloalkyl, cycloalkenyl, heterocycloalkyl, alkenyl, alkynyl, haloalkyl, acyl, halogen, and hydroxylalkyl; and $R_6$ is hydrogen or alkyl.

In a further embodiment, $R_1$ and $R_2$ are independently a halogen such as fluorine, chlorine, bromine or iodine.

In some embodiments, $R_1$ and $R_2$, taken together with the carbon atoms to which they are attached, form a substituted or unsubstituted 5- or 6-membered homocyclic or heterocyclic ring. For example, $R_1$ and $R_2$ may form a methylenedioxy group or aromatic group such as a benzene ring.

In other embodiments, $R_4$ and $R_5$, taken together with the nitrogen atom to which they are attached, form a substituted or unsubstituted 5- or 6-membered heterocyclic ring. For example, $R_4$ and $R_5$ may form a pyrrolidino group.

In preferred embodiments, the small molecule is dehydroisoandrosterone-3-sulfate (DIS), deoxycorticosterone-21 glucoside (DOG), or 3, 4-methylenedioxypyrovalerone (MDPV).

In one embodiment, the subject invention provides methods for developing a new library-immobilized SELEX strategy for the isolation of small-molecule-binding aptamers that can rapidly report binding events through target-induced dye-displacement. In one embodiment, the isolated aptamers bind to specific synthetic cathinones with high target-binding affinity and specificity, for example, MDPV, naphyrone, methylone, pentylone, and mephedrone, which represent a diverse emerging class of drugs of abuse. Such specificity is advantageous in terms of discriminating against structurally-similar non-synthetic cathinone compounds such as amphetamine, methamphetamine, and dopamine as well as common cutting agents such as lidocaine, benzocaine, and caffeine.

In one embodiment, the subject invention provides an aptamer-based sensor for detecting a small-molecule target in a complex sample, comprising an aptamer and a dye, wherein the binding of the dye to the aptamer results in a formation of a three-dimensional architecture able to specifically recognize and report the presence of the small-molecule target. In a further embodiment, the three-dimensional architecture comprises a three-way junction (TWJ) binding domain, wherein the dye binds within the TWJ-binding domain.

The subject invention also provides a method for detecting a small-molecule target in a sample using an aptamer-based sensor selective for the small-molecule target, wherein the aptamer-based sensor comprises an aptamer and a dye that binds to a TWJ-binding domain of the aptamer. Binding of a small-molecule target to the TWJ-binding domain of the aptamer displaces the dye, generating a signal that can be used for detection of the small-molecule target and quantitative measurement of target concentration.

In a preferred embodiment, the dye is diethylthiotricarbocyanine (Cy7). Cy7 binding to hydrophobic DNA TWJ structures occurs in a sequence-independent manner and this interaction produces a distinctive change in absorbance at 670 nm and 760 nm. This allows for the design of a DNA TWJ-structured library which can be used to isolate aptamers that undergo target-binding-induced dye-displacement via SELEX. These aptamers can then be directly employed to optically report the presence of their respective target through displacement of Cy7. Importantly, the absorbance of Cy7 at 670 nm and 760 nm exhibits minimal overlaps with other small molecules or sample matrices, thereby facilitating interference-free detection in complex specimens. SEQ ID NO: 17 is a TWJ-containing structured DNA aptamer enriched pool contemplated for use according to the subject invention.

In one embodiment, the aptamer-based sensor is a DNA aptamer specific for synthetic cathinones with high target-binding affinity and specificity. Preferably, the DNA aptamer is specific for MDPV. In a specific embodiment, the isolated aptamer retains a TWJ-structured binding domain and has a $K_D$ of 6.1 µM. The addition of MDPV displaces Cy7 from the TWJ domain, resulting in a change in the absorbance of this dye.

In one embodiment, the MDPV-binding aptamer, and colorimetric assays provided according to the subject invention can be used for rapid onsite detection of a variety of synthetic cathinones, for example, in seized substances.

BRIEF DESCRIPTION OF DRAWINGS

FIGS. 1A-1C show Cy7 binding to a TWJ-containing structured DNA pool in a sequence-independent manner. (1A) Chemical structure of Cy7 and the sequence of the randomized TWJ pool (SEQ ID NO: 3). (1B) When combined with the TWJ pool, the absorbance of Cy7 monomer (760 nm) and dimer (670 nm) is enhanced. In contrast, when combined with a 1:1:1 mixture of the isolated S1, S2, and S3 stem-loops, only the absorbance of the dimer is enhanced. (1C) Binding stoichiometry of Cy7 monomer to the TWJ pool as characterized by a Job plot.

FIGS. 2A-2C show characterization of target displacement of Cy7 from the aptamers with a TWJ-structured binding domain. (2A) Chemical structure of dehydroisoandrosterone-3-sulfate (DIS) and deoxycorticosterone-21 glucoside (DOG) and structure of their respective aptamers, DISS.1 (SEQ ID NO: 1) and DOGS.1 (SEQ ID NO: 2). Both aptamers contain a TWJ-structured binding domain. The absorbance spectra of the mixture of 3 µM Cy7 and 7 µM (2B) DISS.1 or (2C) DOGS.1 in the absence or presence of 250 µM target. The significant reduction of Cy7 absorbance at 760 nm indicates successful target displacement of Cy7 from the aptamer TWJ binding domain.

FIGS. 3A-3B show characterization of Cy7 binding to the isolated stems from the TWJ pool. (3A) Sequences of the TWJ pool (SEQ ID NO 3), the isolated S1 (SEQ ID NO: 5), S2 (SEQ ID NO: 6), and S3 stem-loops (SEQ ID NO: 7). (3B) Binding of Cy7 to each isolated stem-loop. When 2 µM Cy7 is combined with 10 µM S1 stem-loop, only the absorbance of the dimer (670 nm) increases. Combination with either 10 µM S2 stem-loop or S3 stem-loop does not significantly enhance the absorbance of either the monomer or the dimer. The dashed line represents the spectrum of Cy7 alone.

FIGS. 4A-4B show characterization of Cy7 binding to the TWJ pool. (4A) Titration of increasing amounts of the TWJ pool (2-10 µM) into 2 µM Cy7 resulted in enhanced absorbance of Cy7 at 760 nm, indicating interaction between the TWJ pool and Cy7 monomer. The dashed line represents the spectrum of Cy7 alone. (4B) Cy7 binding affinity for the TWJ pool is estimated from absorbance at 760 nm in the absence and presence of different concentrations of TWJ pool.

FIGS. 9A-9C show detection of MDPV with a label-free Cy7-displacement colorimetric assay. (9A) Cy7 binds within the TWJ domain of MA (SEQ ID NO: 12) (left). The target displaces Cy7 from the binding domain (right) to generate a change in the absorbance spectra of Cy7. (9B) UV-vis spectra of 3 µM Cy7 premixed with 7 µM MA in the presence of varying concentrations of MDPV (0, 0.16, 0.31, 0.63, 1.25, 2.5, 5, 10, 20, 40, 80, 160, 320, 640 µM). The increasing concentrations result in decreased absorbance at 760 nm and increased absorbance at 670 nm. (9C) A calibration curve based on the absorbance ratio at 670/760 nm. Inset shows assay performance at a low concentration range. Error bars show standard deviation from three measurements at each concentration.

FIGS. 10A-10C show high cross-reactivity of MA to synthetic cathinone drugs and its high specificity against other structurally similar or dissimilar interfering agents. (10A) Chemical core structure and structures of synthetic cathinones. (10B) Signal gain measurements from the Cy7-displacement assay with 50 µM MDPV, other synthetic cathinones, or interfering agents (structures shown in panel 10C). Error bars show standard deviations from three measurements of each compound tested.

FIGS. 13A-13C show the performance of the strand-displacement fluorescence assay. (13A) Fluorescence spectra obtained from titration of cDNA-Q into a solution of MA-F at different molar ratios (0-2×). Inset shows binding affinity of cDNA-Q to MA-F as estimated from the fluorescence intensity at 668 nm in the absence and presence of different concentrations of cDNA-Q. (13B) Fluorescence spectra obtained from titration of different concentrations of MDPV into 50 nM MA-F and 50 nM cDNA-Q. (13C) Calibration curves obtained for the strand-displacement fluorescence assay. Inset shows assay performance at a low concentration range. Error bars show standard deviation from three measurements at each concentration.

FIGS. 14A-14C show ITC characterization of MDPV binding affinity to (14A) MA-L alone, (14B) cDNA-MA-L complexes (1:1), and (14C) Cy7-MA-L complexes (1:1). The top panels display raw data showing the heat generated from each titration of MDPV. The bottom panels show the integrated heat of each titration after correcting for dilution heat of the titrant.

BRIEF DESCRIPTION OF SEQUENCES

Figure 5:
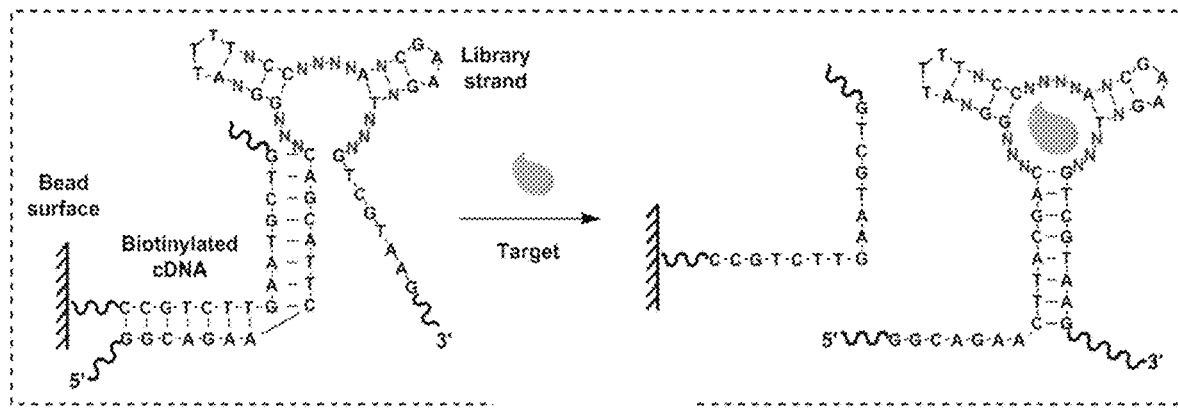
FIG. 5 shows isolation of TWJ-structured aptamers for a Cy7-displacement small-molecule detection assay. A TWJ-containing structured DNA library (SEQ ID NO: 4) is immobilized onto a streptavidin-coated bead surface using a biotinylated cDNA strand (SEQ ID NO: 8) (left). Target-binding strands are eluted due to a conformational change in the aptamer (right).

SEQ ID NO: 1 is the DNA sequence of a DIS binding aptamer contemplated for use according to the subject invention.

SEQ ID NO: 2 is the DNA sequence of a DOG binding aptamer contemplated for use according to the subject invention.

SEQ ID NO: 3 is a randomized TWJ pool contemplated for use according to the subject invention.

SEQ ID NO: 4 is a TWJ-containing structured DNA library contemplated for use according to the subject invention.

SEQ ID NO: 5 is the DNA sequence of a S1 stem-loop contemplated for use according to the subject invention.

SEQ ID NO: 6 is the DNA sequence of a S2 stem-loop contemplated for use according to the subject invention.

SEQ ID NO: 7 is the DNA sequence of a S3 stem-loop contemplated for use according to the subject invention.

SEQ ID NO: 8 is a biotinylated complementary strand for use according to the subject invention.

SEQ ID NO: 9 is a forward primer for use according to the subject invention.

SEQ ID NO: 10 is a reverse primer for use according to the subject invention.

SEQ ID NO: 11 is a biotinylated reverse primer for use according to the subject invention.

SEQ ID NO: 12 is a MDPV binding aptamer contemplated for use according to the subject invention.

SEQ ID NO: 13 is an unlabeled aptamer strand contemplated for use according to the subject invention.

SEQ ID NO: 14 is a fluorophore-labeled aptamer strand contemplated for use according to the subject invention.

SEQ ID NO: 15 is a complementary strand contemplated for use according to the subject invention.

SEQ ID NO: 16 is a quencher-labeled complementary strand contemplated for use according to the subject invention.

SEQ ID NO: 17 is a sequence of aptamer with randomized nucleotides contemplated for use according to the subject invention.

DETAILED DESCRIPTION

The subject invention provides methods, assays and products for detecting small molecules in a sample, in particular, in both clinical and field settings. In one embodiment, the method for detecting a small-molecule target in a sample comprises contacting a sample with an aptamer-based sensor selective for the small-molecule target, and detecting the small-molecule target in the sample.

In one embodiment, the detection of the small-molecule target comprises measuring a signal generated upon binding of the small-molecule target to the aptamer-based sensor. In another embodiment, the method further comprises determining the concentration of the small-molecule target in the sample.

In one embodiment, the sample is a biological sample of a subject. In specific embodiments, the biological sample is selected from blood, plasma, urine, tears, and saliva. The subject may be any animal or human, preferably, a human. The subjects may also be any other animal including, but not limited to, non-human primates, rodents, dogs, cats, horses, cattle, pigs, sheep, goats, chickens, guinea pigs, hamsters and the like.

In one embodiment, the sample is an environmental sample, for example, a water, soil, air, or plant sample. In another embodiment, the sample is a seized drug sample, for instance, a street drug sample seized by law enforcement or government officials.

In one embodiment, the subject invention provides an aptamer-based sensor for detecting a small-molecule target in a complex sample, comprising an aptamer and a dye, wherein binding of the dye to the aptamer results in a formation of a three-dimensional architecture able to specifically recognize and report the presence of the small-molecule target. In a further embodiment, the three-dimensional architecture comprises a TWJ-binding domain, wherein the dye binds within the TWJ-binding domain.

The subject invention also provides a method for detecting a small-molecule target in a sample using an aptamer-based sensor selective for the small-molecule target, wherein the aptamer-based sensor comprises an aptamer and a dye that binds to a TWJ-binding domain of the aptamer. Target binding to the aptamer-based sensor further displaces the dye, generating a signal that can be used for detection of the small-molecule target and, optionally, quantitative measurement of the target concentration.

Small Molecules

The term "small molecule" or "small-molecule target" used herein extends to any molecule capable of being detected using an aptamer technique. In specific embodiments, the small-molecule target may be an amino acid, an amino acid-related molecule, a peptide, a steroid, a lipid, a sugar, a carbohydrate, a biomarker, a drug molecule, a drug metabolite, a coenzyme, a nucleotide, a nucleotide-related molecule, a pyridine nucleotide, a cyclic nucleotide, or a cyclic dinucleotide. In another embodiment, the small-molecule target may be an infective agent, antigen, toxin, disease biomarker and/or specific metal ion.

In one embodiment, the small molecule is a steroid. In a specific embodiment, the steroid is dehydroisoandrosterone-3-sulfate (DIS), or deoxycorticosterone-21 glucoside (DOG).

In one embodiment, the small molecule is a drug molecule. In a further embodiment, the drug molecule is a cathinone, a cathinone derivative, or synthetic cathinone, such as a ring-substituted cathinone derivative or synthetic cathinone.

In one embodiment, the synthetic cathinone may have a general structure of formula (I)

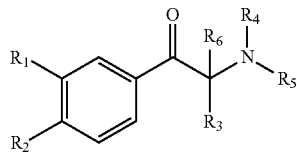

wherein $R_1$, $R_2$, $R_3$, $R_4$, $R_5$, and $R_6$ are each independently selected from the group consisting of hydrogen, alkyl, substituted alkyl, aryl, substituted aryl, benzyl, heteroaryl, substituted heteroaryl, cycloalkyl, substituted cycloalkyl, cycloalkenyl, substituted cycloalkenyl, heterocycloalkyl, alkenyl, alkynyl, alkoxy, thiol, haloalkyl, acyl, halogen, amino, alkylamino, hydroxyl, hydroxylalkyl, and —COOH.

In one embodiment, $R_1$ and $R_2$, are each independently selected from the group consisting of hydrogen, alkyl, aryl, heteroaryl, cycloalkyl, cycloalkenyl, heterocycloalkyl, alkenyl, alkynyl, haloalkyl, acyl, alkoxy, halogen, and hydroxylalkyl; $R_3$ is hydrogen or alkyl. $R_4$, and $R_5$ are each independently selected from the group consisting of hydrogen, alkyl, aryl, heteroaryl, cycloalkyl, cycloalkenyl, heterocycloalkyl, alkenyl, alkynyl, haloalkyl, acyl, halogen, and hydroxylalkyl; and $R_6$ is hydrogen or alkyl.

In a further embodiment, $R_1$ and $R_2$ are independently halogen such as fluorine, chlorine, bromine or iodine.

In some embodiments, $R_1$ and $R_2$, taken together with the carbon atoms to which they are attached, form a substituted or unsubstituted 5- or 6-membered homocyclic or heterocyclic ring. For example, $R_1$ and $R_2$ may form a methylenedioxy group or aromatic ring such as benzene.

In other embodiments, $R_4$ and $R_5$, taken together with the nitrogen atom to which they are attached, form a substituted or unsubstituted 5- or 6-membered heterocyclic ring. For example, $R_4$ and $R_5$ may form a pyrrolidino group.

As used herein, "alkyl" means linear saturated monovalent radicals of at least one carbon atom or a branched saturated monovalent of at least three carbon atoms. It may include hydrocarbon radicals of at least one carbon atom, which may be linear. Examples include, but not limited to, methyl, ethyl, propyl, 2-propyl, n-butyl, iso-butyl, tert-butyl, pentyl, hexyl, and the like.

As used herein, "acyl" means a radical —C(O)R where R includes, but is not limited to, hydrogen, alkyl or cycloalkyl, and heterocycloalkyl. Examples include, but are not limited to, formyl, acetyl, ethylcarbonyl, and the like. An aryl group may be substituted or unsubstituted.

As used herein, "alkylamino" means a radical —NHR or —NR2 where each R is, independently, an alkyl group. Examples include, but are not limited to, methylamino, (1-methylethyl)amino, dimethyl amino, methylethylamino, di(1-methylethyl)amino, and the like. An alkylamino may be substituted or unsubstituted.

As used herein, "hydroxyalkyl" means an alkyl radical substituted with one or more hydroxy groups. Representative examples include, but are not limited to, hydroxymethyl, 2-hydroxyethyl; 2-hydroxypropyl; 3-hydroxypropyl; 1-(hydroxymethyl)-2-methylpropyl; 2-hydroxybutyl; 3-hydroxybutyl; 4-hydroxybutyl; 2,3-dihydroxypropyl; 2-hydroxy-1-hydroxymethylethyl; 2,3-dihydroxybutyl; 3,4-dihydroxybutyl and 2-(hydroxymethyl)-3-hydroxy-propyl, preferably 2-hydroxyethyl, 2,3-dihydroxypropyl and 1-(hydroxymethyl) 2-hydroxyethyl. A hydroxyalkyl may be substituted or unsubstituted.

As used herein, "alkenyl" refers to a straight or branched hydrocarbon chain containing one or more double bonds. The alkenyl group may have 2 to 9 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from ethenyl; propen-1-yl; propen-2-yl; propen-3-yl; buten-1-yl; buten-2-yl; buten-3-yl; buten-4-yl; 1-methyl-propen-1-yl; 2-methyl-propen-1-yl; 1-ethyl-ethen-1-yl; 2-methyl-propen-3-yl; buta-1,3-dienyl; buta-1,2,-dienyl and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain comprising one or more triple bonds. The alkynyl group may have 2 to 9 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, e.g., the alkynyl chain is selected from ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "cycloalkyl" means a fully saturated carbocyclyl ring or ring system. Examples include, but are not limited to, cyclopropyl, cyclobutyl, cyclopentyl, and cyclohexyl.

As used herein, "aryl" refers to a carbocyclic (all carbon) monocyclic or multicyclic aromatic ring system (including fused ring systems where two carbocyclic rings share a chemical bond). The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, phenyl, benzyl, α-naphthyl, β-naphthyl, biphenyl, anthryl, tetrahydronaphthyl, fluorenyl, indanyl, biphenylenyl, and acenaphthenyl. Preferred aryl groups are phenyl and naphthyl.

As used herein, "heteroaryl" refers to an aromatic ring or ring system (i.e., two or more fused rings that share two adjacent atoms) that comprise(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "haloalkyl" refers to an alkyl group in which one or more of the hydrogen atoms is replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, a "substituted" group may be substituted with one or more group(s) individually and independently selected from alkyl, alkenyl, alkynyl, cycloalkyl, cycloalkenyl, cycloalkynyl, benzyl, substituted benzyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiol, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "halogen" refers to an atom of fluorine, chlorine, bromine or iodine.

As used herein, "homocyclic ring" refers to cycloalkyl or aryl.

As used herein, "heterocyclic ring" refers to a ring, which may contain 1 to 4 hetero-atoms selected from among nitrogen, oxygen, sulfur and other atoms in addition to carbon atoms.

Exemplary cathinones or synthetic cathinones include, but are not limited to, 3, 4-methylenedioxypyrovalerone (MDPV), naphyrone, methylone, ethylone, butylone, pentylone, mephedrone, mexedrone, buphedrone, pentedrone, hexedrone, heptedrone, α-pyrrolidinopropiophenone (α-PPP), 4'-methyl-α-pyrrolidinopropiophenone (M-α-PPP), 3',4'-methylenedioxy-α-pyrrolidinopropiophenone (MDPPP), 1-phenyl-2-(1-pyrrolidinyl)-1-pentanone (α-PVP), α-pyrrolidinohexiophenone (α-PHP), α-pyrrolidinoheptiophenone (α-PHpP, PV8), diethylpropion, pyrovalerone, dimethylcathinone, diethyl cathinone, methcathinone, ethcathinone, 3-methylmethcathinone (3-MMC), 4-methyl-ethcathinone (4-MEC), 3-chloromethcathinone (3-CMC), 4-chloromethcathinone (4-CMC). n-ethyl-nor-pentedrone (NEP), n-ethyl-nor-hexedrone (Hexen), n-ethyl-nor-heptedrone, 4-ethylpentedrone, 4-methyl-NEP, and n-ethyl-nor-pentylone.

In a specific embodiment, the synthetic cathinone is MDPV, naphyrone, methylone, pentylone, or mephedrone.

Aptamers

The subject invention provides aptamer-based sensors for detecting small-molecule targets. Aptamers are nucleic acid molecules characterized by the ability to bind to a target molecule with high specificity and high affinity. Almost every aptamer identified to date is a non-naturally occurring molecule. Aptamers to a given target may be identified and/or produced by the method of systematic evolution of ligands by exponential enrichment (SELEX). In one embodiment, the aptamer according to the subject invention is isolated by SELEX for the small molecule of interest. In a further embodiment, the aptamer is isolated by SELEX for MDPV and numerous members of the synthetic cathinone family, including, but not limited to, naphyrone, methylone, pentylone, and mephedrone.

In one embodiment, the aptamer is an oligonucleotide, such as DNA or RNA molecules and may be single-stranded or double-stranded. In a preferred embodiment, the aptamer is a DNA aptamer.

The aptamer can form various secondary structures (e.g., stems, loops, bulges, pseudoknots, G-quadruplexes and kissing hairpins), which in turn can form unique three-dimensional architectures able to specifically recognize their targets by exploiting a variety of interactions—such as hydrophobic and electrostatic interactions, hydrogen bonding, van der Waals forces and π-π stacking as well as shape complementarity.

As used herein, the terms "polynucleotide," "nucleotide," "oligonucleotide," and "nucleic acid" can be used interchangeably to refer to a nucleic acid comprising DNA, RNA, derivatives thereof, or combinations thereof.

In one embodiment, the aptamer according to the present invention may comprise at least 10, at least 20, at least 30, at least 40, at least 50, at least 60, at least 70, or at least 80 nucleotides. The aptamer according to the present invention, preferably, comprises 10 to 200 nucleotides, preferably 15 to 150 nucleotides, more preferably 20 to 100 nucleotides.

In one embodiment, the aptamer according to the present invention may have a minimum length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The aptamer according to the present invention may have a maximum length of, for example, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides. The aptamer according to the present invention may have a length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In some embodiments, the aptamers according to the subject invention may have free ends. For example, the 3' and 5' ends may not be ligated to form a loop, although they may be conjugated to other molecules or otherwise modified. The aptamers may adopt a tertiary structure such as a hairpin loop. In some embodiments, the aptamers may be looped. For example, the 5' and 3' ends of the nucleic acid are covalently bonded to form a loop not having any free ends.

In one embodiment, the aptamer according to the subject invention comprises at least one stems, two stems, or three stems. Preferably, the aptamer comprises three stems. Each stem may be fully or partially complementary. Each stem may comprise the same or a different number of nucleotides. Exemplary lengths of each stem may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides.

In one embodiment, the aptamer comprises at least one junction, which is formed when two or more stems meet. In certain embodiments, the junction may be a loop between two stems, or a three-way junction (TWJ). The junction may comprise, for example, 5, 6, 7, 8, 9, 10, 11, 12, 13, 14, 15, 16, 17, 18, 19, 20, 21, 22, 23, 24, 25, 26, 27, 28, 29, or 30 nucleotides. The junction in an aptamer can serve as a binding domain for a small-molecule target. In a specific embodiment, the aptamer comprises one TWJ-binding domain. In some embodiments, the aptamer may be a monomer, dimer, trimer, or tetramer. Such aptamer can comprise one, two, three, or four TWJ-binding domains.

The aptamers of the present invention may or may not include chemical modifications. The chemical modifications as described herein include a chemical substitution at a sugar position, a phosphate position, and/or a base position of the nucleic acid including, for example, incorporation of a modified nucleotide, incorporation of a capping moiety (e.g., 3' capping), conjugation to a high molecular weight, non-immunogenic compound (e.g., polyethylene glycol (PEG)), conjugation to a lipophilic compound, and substitutions in the phosphate backbone. Base modifications may include 5-position pyrimidine modifications, modifications at exocyclic amines, substitution of 4-thiouridine, substitution of 5-bromo- or 5-iodo-uracil, and backbone modifications. Sugar modifications may include 2'-amine nucleotides (2'-NH2). 2'-fluoronucleotides (2'-F), and 2'-O-methyl (2'-OMe) nucleotides. Such modifications may improve the stability of the aptamers or make the aptamers more resistant to degradation. In some embodiments, each base of a given type (e.g., A, T, C, and G) may contain the same chemical modification.

The aptamers may or may not be modified by addition of one or more reporter labels (or detectable labels). In some embodiments, the label may be attached to either the 5' or 3' end of the aptamer. The label may also be attached with the backbone of the aptamer. The skilled person will be aware of techniques for attaching labels to nucleic acid strands. The detectable label may be attached directly or indirectly to the nucleic acid aptamer. If the label is indirectly attached to the nucleic acid aptamer, it may be by any mechanism known to one of skill in the art, such as using biotin and streptavidin.

The aptamers may or may not comprise a reporter label, such as a fluorescent dye, nanoparticle, or an enzyme. Exemplary labels include, but are not limited to, an organic donor fluorophore or an organic acceptor fluorophore, a luminescent lanthanide, a fluorescent or luminescent nanoparticle, an affinity tag such as biotin, or a polypeptide. In some embodiments, the aptamer may comprise a fluorescent label, for example, fluorescein, TAMRA, rhodamine, Texas Red, Alexa Fluor (e.g., AlexaFluor 488, AlexaFluor 532, AlexaFluor 546, AlexaFluor 594, AlexaFluor 633 and AlexaFluor 647), cyanine dye (e.g., Cy7, Cy7.5, Cy5, Cy5.5 and Cy3), Tye dye (e.g., TYE 563, TYE 665, TYE 705), atto dye (e.g., Atto 594 and Atto 633), Hexachlorofluorescein, FAM (6-carboxyfluroescein), BODIPY FL, OliGreen, 40,6-diamidino-2-phenylindol (DAPI), Hoechst 33,258, malachite green (MG), and FITC. The nanoparticle can be an upconversion nanoparticle. In some embodiments, the fluorophore is selected from the group consisting of fluorophores that emit a blue, green, near red or far red fluorescence.

In some embodiments, the aptamer may bind to a complementary sequence. The aptamer and the complementary sequence may be labeled by a fluorescent dye and quencher pair. In certain embodiments, a fluorophore is conjugated at one end of the aptamer and a quencher at one end of the complementary sequence. In the absence of its target, the complementary sequence binds to the aptamer, thereby positioning the fluorophore close to the quencher. Target binding to the aptamer displaces the complementary sequence, resulting the separation of the fluorophore and the quencher. The resulting recovery of the fluorescence signal directly reflects the extent of the binding and can be used for detection and quantitative measurement of the target concentration.

The quenchers can be, for example, Dabcyl, DDQ-I, Eclipse, Iowa Black FQ, BHQ-1, QSY-7, BHQ-2, DDQ-II, Iowa Black RQ, QSY-21, or BHQ-3.

In some embodiments, the fluorophore is at a location of, for example, $1^{st}$, $2^{nd}$, $3^{rd}$, $4^{th}$, $5^{th}$, $6^{th}$, $7^{th}$, $8^{th}$, $9^{th}$, or $10^{th}$ nucleotide from either 5' end or 3' end of the aptamer. The quencher is at a location of, for example, $1^{st}$, $2^{nd}$, $3^{rd}$, $4^{th}$, $5^{th}$, $6^{th}$, $7^{th}$, $8^{th}$, $9^{th}$, or $10^{th}$, nucleotide from either 3' end or 5' end of the complementary sequence.

In preferred embodiments, the location of the fluorophore and quencher-conjugated is such that the proximity of fluorophore and quencher in a complementary sequence binding conformation provide maximal quenching and the fluorophore and quencher in a separated conformation provide maximal fluorescence of the fluorophore. For optimized detection of fluorescence changes that allows utilization of aptamers for target detection, it is desirable that the fluorescence in the quenched conformation is as low as possible and the fluorescence in the unquenched conformation is as high as possible combined with the most rapid interconversion from one conformation to the other.

In one embodiment, the aptamer can bind a dye such as a fluorophore with the three-way junction binding domain. In a preferred embodiment, the dye is diethylthiatricarbocyanine (Cy7).

In one embodiment, the aptamer has inherent dye-displacement functionality. A dye can bind within the three-way junction binding domain of the aptamer and the dye can be displaced in the presence of the small-molecule target, resulting in a change in absorbance. Such change may occur within seconds. Such change can also directly reflect the extent of target binding and be used for detection and quantitative measurement of the target concentration.

In a specific embodiment, the aptamer specifically recognizes the core structure of synthetic cathinones (e.g., formula (I)) rather than their side chain substituents.

Method of Isolating the Aptamer

In one embodiment, the subject invention provides an aptamer-based sensor for detecting a small-molecule target in a complex sample. The aptamer-based sensor according to the subject invention comprises an aptamer and a dye, wherein the aptamer comprises a TWJ-binding domain selective for a small-molecule target, and wherein the dye binds within the TWJ-binding domain.

In one embodiment, the subject invention provides a method of isolating aptamers with dye-displacement functionality that are selective for small molecules. The aptamer with dye-displacement functionality may be isolated from a SELEX aptamer library.

In one embodiment, the SELEX aptamer library is a DNA or RNA sequence that forms a structure comprising three stems and a three-way junction (TWJ) binding domain when binding to a small-molecule target, wherein the small-molecule target binds within the TWJ-binding domain. In one embodiment, the SELEX aptamer library comprises at least 2, 3, 4, 5, 6, 7, 8, 9, 10, 11, 12, 13, 14, 15, 16, 17, 18, 19, 20 randomized nucleotides. Preferably, the randomization of nucleotides occurs in the TWJ-binding domain.

In some embodiments, randomizations may occur in the adjacent sequences to the TWJ-binding domain of the SELEX aptamer library. Changes in the sequence adjacent to the TWJ-binding domain may affect the affinity of the aptamer. In a preferred embodiment, randomization of one base-pair in both stems 2 and 3 of the aptamer library enhances the potential target-binding affinity of the aptamer.

In one embodiment, the nitrogenous base of the randomized DNA/RNA nucleotides are each independently selected from adenine (A), thymine (T), cytosine (C), guanine (G), and uracil (U).

In one embodiment, the TWJ-structured SELEX library may be chemically modified, preferably at the 3' and/or 5' end. The chemical modifications may include, for example, a chemical substitution at a sugar position, a phosphate position, and/or a base position of the nucleic acid, including, but not limited to, incorporation of a modified nucleotide, incorporation of a capping moiety (e.g., 3' capping), conjugation to a high molecular weight, non-immunogenic compound (e.g., polyethylene glycol (PEG)), conjugation to a small molecule such as biotin or fluorescein, and conjugation to lipophilic compounds.

In one embodiment, the binding of Cy7 monomer to TWJs of aptamers is structure-selective and sequence-independent, making it possible to isolate new small-molecule-binding aptamers with intrinsic dye-displacement functionality from a TWJ-structured SELEX aptamer library.

In one embodiment, the method for isolating an aptamer with dye-displacement functionality that is selective for a small-molecule target comprises providing an aptamer library, wherein the aptamer library is a TWJ-structured SELEX aptamer library, immobilizing the aptamer library, providing a small-molecule target, isolating the aptamer selective for the small-molecule target.

In a further embodiment, the aptamer library is immobilized onto a surface and the aptamer selective for the target of interest is then mobilized upon target binding. In a specific embodiment, the aptamer library is immobilized onto the surfaces of streptavidin-coated beads using a biotinylated cDNA strand, which disrupts the TWJ structure of the library. In the presence of the small-molecule target, library aptamers undergo a conformational change and refold to form TWJ structures. Thus, target-specific aptamer strands can be eluted due to a conformational change upon target binding.

In one embodiment, the SELEX aptamer library according to the present invention may have a minimum length of, for example, 40, 45, 50, 55, 60, 65, 70, 75, 80, 85, 90, 95, or 100 nucleotides. The SELEX aptamer library according to the present invention may have a maximum length of, for example, 100, 105, 110, 115, 120, 125, 130, 135, 140, 145, 150, 155, 160, 165, 170, 175, 180, 185, 190, 195, or 200 nucleotides. In a specific embodiment, the TWJ-structured SELEX library has a sequence of SEQ ID No: 4. The isolated TWJ-structured aptamer pool can have a sequence of SEQ ID No. 3.

In some embodiments, the aptamers are selective for synthetic cathinones, such as MDPV. Preferably, the aptamer comprises three fully complementary stems. In a specific embodiment, stem 1 has a sequence of SEQ ID No: 5; stem 2 has a sequence of SEQ ID No: 6; and stem 3 has a sequence of SEQ ID NO: 7.

In a preferred embodiment, the aptamer is a DNA aptamer comprising 46 nucleotides. Preferably, the randomization of nucleotides occurs in the TWJ binding domain, for example, at $9^{th}$, $10^{th}$, $11^{th}$, $14^{th}$, $20^{th}$, $23^{rd}$, $24^{th}$, $25^{th}$, $26^{th}$, $28^{th}$, $34^{th}$, $36^{th}$, $37^{th}$, and/or $38^{th}$ nucleotide from 5' end of the aptamer and any combination thereof.

In a specific embodiment, the aptamer is MA having a sequence of SEQ ID No: 12, or a sequence sharing at least 50%, 55%, 60%, 65%, 70%, 75%, 80%, 85%, 90%, 95% or 99% identity with SEQ ID No: 12.

In one embodiment, the aptamer binds to the small molecule with a dissociation constant of, for example, about 1 μM, about 2 μM, about 3 μM, about 4 μM, about 5 μM, about 6 μM, about 7 μM, about 8 about 9 μM, or about 10 μM.

In some embodiments, the aptamer MA does not bind to various structurally similar illicit drugs such as amphetamine and methamphetamine or common cutting agents such as lidocaine, benzocaine, and caffeine.

Method of Using the Aptamer

The subject invention also provides methods of using the aptamer-based sensor for detecting a small-molecule target in a complex sample. In one embodiment, the subject invention provides an assay employing dye-displacement strategies for the detection of small-molecule targets. In such assay, a small-molecule dye is initially associated with the binding domain of an aptamer. The presence of the small-molecule target causes displacement of the dye from the binding domain, resulting in a change in the absorbance or fluorescence of the dye.

Advantageously, because the aptamers typically bind to these small-molecule targets and dyes with similar affinities, target-induced dye-displacement is more thermodynamically feasible than the displacement of a tightly-bound complementary strand. As a result, dye-displacement assays can achieve a detection limit that is at least 10-fold lower than the $K_D$ of the aptamer.

In one embodiment, the aptamer according to the subject invention does not require any additional labeling or chemical modification. The methods for detecting small molecule targets using such aptamer without further labeling are label-free.

In one embodiment, the subject invention provides a method for rapid and sensitive detection of a small-molecule target in a sample comprising contacting the sample with a aptamer-based sensor selective for the small-molecule target, wherein the aptamer-based sensor is a aptamer with a dye binding to the TWJ-binding domain, and detecting the small-molecule target in the sample, wherein the detection of the small-molecule target comprises measuring a signal generated upon binding of the small-molecule target to the TWJ-binding domain of the aptamer.

In some embodiments, the signal generated has optical properties selected from the group consisting of: light reflectivity, color, the fluorescence emission wavelength(s) and the fluorescence emission intensity. Preferably, the signal is a change in absorbance or fluorescence intensity.

In a specific embodiment, the dye is Cy7. The signal generated is the change in Cy7 absorbance upon displacement of Cy7 monomer by a small-molecule target from the TWJ-binding domain. Such change comprises a reduction of absorbance at 760 nm and enhancement of absorbance at 670 nm. In certain embodiments, the signal change is indicated using the absorbance ratio at 670/760 nm.

In another embodiment, the method further comprises determining the concentration of the small-molecule target in the sample. The determination can comprise comparing the signal generated upon target binding with a standard curve of such signal. For example, the determination based on Cy7 displacement assay comprises comparing the absorbance signal generated upon binding of aptamer-target complex with a standard curve of the absorbance of Cy7, or a standard curve of the absorbance ratio at 670/760 nm. The absorbance read-out can be quantified in seconds by, for example, a microplate-reader or portable photometer, allowing for high-throughput or on-site detection, respectively.

In a specific embodiment, the aptamer is selective for synthetic cathinones, such as MDPV. The aptamer is a DNA aptamer comprising 46 nucleotides. In a preferred embodiment, the aptamer is MA having a sequence of SEQ ID No: 12. Advantageously, binding of MA with Cy7 within its three-way junction binding domain can be displaced in the presence of MDPV efficiently, resulting in a change in Cy7 absorbance. MA can recognize molecules that share the same beta-keto phenethylamine core structure as MDPV but with different side-chains.

In one embodiment, the method according to the subject invention can achieve superior sensitivity for target detection at low micromolar or nanomolar concentration, for example, as low as about 200 μM, about 150 μM, about 100 μM, about 10 μM, about 1 μM, about 100 nM, about 10 nM, or about 1 nM. In another embodiment, the method according to the subject invention can achieve target sensitivity at a low concentration of about 300 nM.

In one embodiment, the methods for small molecule detection provided herein are rapid and can be completed in about 5 minutes to about 120 minutes, about 6 minutes to about 110 minutes, about 7 minutes to about 100 minutes, about 8 minutes to about 90 minutes, about 9 minutes to about 80 minutes, about 10 minutes to about 70 minutes about 15 minutes to about 60 minutes, about 20 minutes to about 50 minutes, or about 25 minutes to about 40 minutes. In some embodiments, the method can be completed in about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, or about 120 minutes.

In another embodiment, the methods for small molecule detection provided herein are rapid and can be completed in about 5 seconds to about 5 minutes, about 10 seconds to about 4 minutes, about 15 seconds to about 3 minutes, about 20 seconds to about 2 minutes, or about 25 seconds to about 1 minute.

In one embodiment, the methods and assays according to the subject invention can detect MDPV at concentrations as low as 300 nM with strong cross-reactivity to other synthetic cathinone analogs but not for various interferents and structurally-similar non-cathinone compounds.

In one embodiment, the methods using an aptamer-based sensor are able to detect MDPV at a concentration as low as 300 nM, 20 times lower than the $K_D$ of the aptamer, within seconds.

Advantageously, the Cy7-displacement assay is more sensitive and rapid than a strand-displacement fluorescence assay, which uses a fluorophore-modified version of the same aptamer along with a quencher-modified complementary strand.

In one embodiment, the subject invention provides a method for detecting small molecules that are biomarkers for diagnosis of a disease or condition, or monitoring therapeutic response to specific treatments. In specific embodiments, the condition can be, for example, cancer, an injury, an inflammatory disease or a neurodegenerative disease. In some embodiments, the condition can be substance abuse, psychosis, schizophrenia, Parkinson's disease, attention deficit hyperactivity disorder (ADHD), and pain. In some embodiments, the pain is acute pain or chronic pain. In some embodiments, the pain is neuropathic pain, e.g., chronic neuropathic pain.

In one embodiment, the methods, assays, and products according to the subject invention will accelerate the development of sensitive and accurate sensors for detecting small-molecule targets in fields including environmental monitoring, food safety, law enforcement, medical diagnostics, and public health.

The subject invention encompasses the use of sequences having a degree of sequence identity or sequence similarity with the nucleic acid sequence(s) of the present invention. A similar sequence is taken to include a nucleotide sequence which may be at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%. 78%, 79%, 80%, 81%, 82%, 83%, 84%, 85%, 86%, 87%, 88%, 89%, 90%, 91%, 92%, 93%, 94%. 95%, 96%, 97%, 98%, or 99% identical to the subject sequence. Typically, the similar sequences will comprise the same or similar secondary structure as the subject nucleic acid aptamer. In one embodiment, a similar sequence is taken to include a nucleotide sequence which has one or several additions, deletions and/or substitutions compared with the subject sequence.

EXAMPLES

Experimental Section
Materials.

All oligonucleotides were ordered from Integrated DNA Technologies (IDT), purified with HPLC, and dissolved in PCR quality water (Invitrogen). DNA concentrations were measured using a NanoDrop 2000 spectrophotometer (Thermo Scientific). Diethylthiatricarbocyanine (Cy7), dehydroisoandrosterone-3-sulfate (DIS) sodium salt dihydrate, deoxycorticosterone-21 glucoside (DOG) and all other chemicals were purchased from Sigma-Aldrich unless otherwise noted. Drug standards, including 3,4-methylenedioxypyrovalerone (MDPV), mephedrone, methylone, naphyrone, and pentylone were purchased from Cayman Chemicals. Tween 20 and formamide were purchased from Fisher Scientific. Streptavidin-coated agarose resin (1-3 mg biotinylated BSA/ml resin), One Shot Chemically Competent E. coli, and SYBR Gold were purchased from Thermo Scientific. 500 μL micro-gravity columns were purchased from BioRad.

SELEX Procedure.

The isolation of MDPV-binding aptamers followed a previously-reported SELEX method[9] with some modifications. Briefly, during each round of SELEX, 100 pmole of either the TWJ-containing library or the enriched pool from a given round was mixed with 500 pmole of biotinylated complementary strand (cDNA-bio) in 250 μL selection buffer (10 mM Tris-HCl, 0.5 mM MgCl$_2$, 20 mM NaCl, pH 7.4). The mixture was heated at 95° C. for 5 min, slowly cooled to room temperature over 30 min, and then loaded into a micro-gravity column containing 250 μL of streptavidin-coated agarose resin for library immobilization. The library-immobilized column was washed with selection buffer at least 10 times to remove unconjugated library and complementary strands. Target-bound aptamers were eluted using 250 μL, of 100 nM (Rounds 1-5) or 50 nM (Rounds 6-10) MDPV in selection buffer. The eluted aptamers were concentrated using a 3K molecular weight cut-off spin filter (Millipore) and mixed with 1 μM forward primer (Table 1, FP) and 1 μM biotinylated reverse primer (Table 1, RP-bio) in 1 mL GoTaq Hot Start Master Mix (Promega). Polymerase chain reaction (PCR) was then performed using a BioRad C1000 thermal cycler. Amplification conditions were as follows: 1 cycle of 95° C. for 2 min; 13 cycles of 95° C. for 15 s, 58° C. for 30 s, and 72° C. for 45 s; and 1 cycle of 72° C. for 2 min. The double-stranded PCR product was immobilized on a micro-gravity column containing 200 μL of streptavidin-coated agarose resin. The column was washed five times with 200 μL 10 mM Tris-HCl buffer (pH 7.4) containing 20 mM NaCl to remove unconjugated strands, and then incubated with 300 μL 0.2 M NaOH for 10 mM. Finally, the eluent was collected and neutralized with 0.2 M HCl in a 1.5 mL microcentrifugation tube and concentrated using a 3K molecular weight cut-off spin filter. The enriched pool was used for next round of SELEX after its concentration was measured using a NanoDrop 2000.

DNA core facility. Multiple sequence alignments were carried out using BioEdit software, and the sequence logo was generated using WebLogo.[10]

Cy7-Displacement Assay for Detection of MDPV.

5 μL MA (final concentration: 7 μM), 5 μL Cy7 (final concentration: 3 μM), 5 μL of varying concentrations of MDPV, and 35 μL reaction buffer (10 mM Tris-HCl, 0.5 mM $MgCl_2$, 20 mM NaCl, 0.01% Tween 20, 1% DMSO, pH 7.4) were mixed in wells of a 384-well plate. UV-vis spectra were immediately recorded from 450-900 nm using a Tecan

TABLE 1

| Sequence ID No | Sequence ID | Sequence (5'-3') |
|---|---|---|
| SEQ ID NO: 1 | DISS.1 | CTCGGGACGTGGATTTTCCGCATACGAAGTTGTCCCGAG |
| SEQ ID NO: 2 | DOGS.1 | TCGGGACGTGGATTTTCCACAAACCAGAATGGTGTCCCGA |
| SEQ ID NO: 3 | TWJ pool | CTTACGACNNNGGCATTTTGCCNNNNAACGAAGTTNNNGTCGTAAG |
| SEQ ID NO: 4 | Library | CGAGCATAGGCAGAACTTACGACNNNGGNATTTTNCCNNNNANCGAAGNTNNNGTCGTAAGAGCGAGTCATTC |
| SEQ ID NO: 5 | S1 stem-loop | CTTACGACTTTGTCGTAAG |
| SEQ ID NO: 6 | S2 stem-loop | GGCATTTTGCC |
| SEQ ID NO: 7 | S3 stem-loop | AACGAAGTT |
| SEQ ID NO: 8 | cDNA-bio | TTTTTGTCGTAAGTTCTGCCATTTT/Bio/ |
| SEQ ID NO: 9 | FP | GCAGCATAGGCAGAACTTAC |
| SEQ ID NO: 10 | RP | GAATGACTCGCTCTTACGAC |
| SEQ ID NO: 11 | RP-bio | /Bio/GAATGACTCGCTCTTACGAC |
| SEQ ID NO: 12 | MA | CTTACGACTCAGGCATTTTGCCGGGTAACGAAGTTACTGTCGTAAG |
| SEQ ID NO: 13 | MA-L | CAGAACTTACGACTCAGGCATTTTGCCGGGTAACGAAGTTACTGTCGTAAG |
| SEQ ID NO: 14 | MA-F | /5Cy5/GGCAGAACTTACGACTCAGGCATTTTGCCGGGTAACGAAGTTACTGTCGTAAG |
| SEQ ID NO: 15 | cDNA | GTCGTAAGTTCTGCC |
| SEQ ID NO: 16 | cDNA-Q | GTCGTAAGTTCTGCC/3IAbRQsp/ | a. N represents random base
b. /Bio/ represents biotin modification
c. /5Cy5/ represents Cy5 fluorophore modification
/3IAbRQsp/ represents Iowa Black RQ quencher modification Counter-SELEX was performed against methamphetamine (Rounds 4-5), amphetamine (Rounds 6-7) and dopamine (Rounds 8-10). Specifically, the library-immobilized column was washed 10 times with 250 μL of 100 μM counter-SELEX target in selection buffer, followed by 20 times with 250 μL selection buffer prior to target elution.

Cloning and Sequencing.

After 10 rounds of SELEX, the final enriched pool was PCR amplified with unlabeled forward and reverse primers (Table 1, FP and RP) under the same conditions described in the SELEX procedure with a prolonged 30-min extension step at 72° C. to add an A-tail. The PCR product was cloned into E. coli using the TOPO TA cloning kit (Invitrogen). 50 colonies were randomly picked and sequenced at the FIU Infinite M1000 PRO at room temperature. Signal gain was calculated by $(R-R_0)/R_0$, where $R_0$ and R are the 670 nm/760 nm absorbance ratio without and with MDPV, respectively. The same assay was performed with 50 μM and 250 μM of naphyrone, methylone, pentylone and mephedrone to evaluate the cross-reactivity of the assay. Additionally, we tested the specificity of the assay using interfering agents such as amphetamine, methamphetamine, dopamine, lidocaine, benzocaine, and caffeine.

Characterization of Target Displacement of Cy7 from TWJ-Structured Aptamers.

5 μL DISS.1 aptamer or DOGS.1 aptamer (final concentration: 7 μM), 5 μL Cy7 (final concentration: 3 μM), 5 μL of target (final concentration: 0 or 250 μM), and 35 μL selection buffer[1] (20 mM Tris-HCl, 10 mM $MgCl_2$, 1 M NaCl, 0.01% Tween 20, 1% DMSO, pH 7.4) were mixed in wells of a 384-well plate. UV-vis spectra were immediately recorded from 450-900 nm using a Tecan Infinite M1000 PRO at room temperature.

Characterization of Binding of Cy7 to TWJ Pool.

5 µL of different concentrations of TWJ pool, 5 µL of 20 µM Cy7, and 40 µL, reaction buffer (final concentration 10 mM Tris-HCl, 0.5 mM $MgCl_2$, 20 mM NaCl, 0.01% Tween 20, and 1% DMSO, pH 7.4) were mixed in wells of a 384-well plate. UV-vis spectra were immediately recorded from 450 nm to 900 nm at room temperature. The absorbance value at 760 nm was plotted against the concentration of added TWJ pool. The $K_D$ was estimated by non-linear fitting using the Langmuir equation.

Continuous Variation Experiment (Job Plot).

10 µM Cy7 and 10 µM TWJ pool were separately prepared in reaction buffer. Different ratios of Cy7 and TWJ pool were then mixed, with the concentration of both species totaling 10 µM. 50 µL of each mixture was loaded into a 384-well plate, and UV-vis spectra were immediately recorded from 450-900 nm at room temperature. The absorbance at 760 nm was plotted versus the mole fraction of Cy7.

Development of a Target Elution Assay to Assess Pool Affinity and Target Specificity.

After each round of SELEX, 50 pmole of the enriched pool was mixed with 250 pmole of biotinylated complementary strand (Table 1, cDNA-bio) in 125 µL binding buffer (10 mM Tris-HCl, 0.5 mM $MgCl_2$, 20 mM NaCl, 0.01% Tween 20%, pH 7.4). The mixture was heated to 95° C. for 5 min, slowly cooled down to room temperature over 30 min, and loaded into a micro-gravity column containing 125 µL of streptavidin-coated agarose resin for library immobilization. The library-immobilized resin was collected into a microcentrifugation tube and washed five times with 625 µL binding buffer on an end-to-end rotator to remove unconjugated library and complementary stands. After washing, the library-conjugated resin was re-suspended in 150 µL binding buffer and aliquoted into six PCR tubes (20 µL each). 50 µL binding buffer containing different amounts of MDPV was added to these tubes to reach final target concentrations of 0, 10, 50, 100, 250, and 500 µM. After a 60-min incubation on an end-over-end rotator, the agarose resin was precipitated by centrifugation. 3 µL of supernatant was collected and mixed with 6 µL, of gel loading buffer (75% formamide, 10% glycerol, 0.125% SDS, 10 mM EDTA, and 0.15% (w/v) xylene cyanol). 5 µL of each collected sample was then loaded into the wells of a 15% denaturing polyacrylamide gel. A control sample (40 nM initial random library) was also loaded into the gel to evaluate the concentration of target-eluted library in each sample. Separation was carried out at 20 V/cm for 1 hour in 0.5×TBE running buffer. The gel was stained with 1×SYBR Gold solution for 25 min and imaged using a ChemiDoc MP Image System (Bio-Rad). The percentages of elution were calculated from the concentration of target-eluted library and the initial amount of library used in immobilization, which were then plotted versus the concentration of MDPV. $K_D$ of the library pool was estimated with non-linear curve fitting using the Langmuir equation. The target specificity for the enriched pool was tested using the method described above, by eluting library-immobilized agarose resin with binding buffer, 500 µM MDPV, 500 µM methamphetamine, 500 µM amphetamine, and 500 µM dopamine.

Isothermal Titration Calorimetry (ITC) Experiments.

All ITC experiments were performed at 23° C. in selection buffer with (for experiments involving Cy7) or without (for experiments not involving Cy7) 5% DMSO with a MicroCal iTC200 instrument (Malvern). The sample cell contained 20 µM MA, 20 µM MA-L, 20 µM Cy7-MA complex (1:1), 20 µM Cy7:MA-L complex (1:1), or 20 µM cDNA:MA-L complex (1:1). The syringe contained 1 mM MDPV in selection buffer with or without DMSO. Each experiment consisted of an initial 0.4 µL purge injection followed by 19 successive 2 µL injections with spacing of 180 seconds to a final molar ratio of 11:1 (MDPV:aptamer). The raw data were first corrected based on the heat of dilution of target, and then analyzed with the MicroCal analysis kit integrated into Origin 7 software with a single-site binding model.

Strand-Displacement Fluorescence Assay for Detection of MDPV.

First, the molar ratio between the fluorophore-labeled aptamer strand (Table 1, MA-F) and the quencher-labeled complementary strand (Table 1, cDNA-Q) was optimized. Specifically, 8 µL of MA-F (final concentration 50 nM) and 8 µL of different concentrations of cDNA-Q were mixed with selection buffer to a total volume of 80 µL The samples were then heated at 95° C. for 5 min and slowly cooled down to room temperature over 30 min. 75 µL of samples were loaded into a 384-well plate, and the fluorescence spectra were recorded from 655-850 nm with excitation at 648 nm at room temperature. To perform the strand-displacement fluorescence assay, selection buffer containing 50 nM MA-F and 50 nM cDNA-Q (final concentration) was heated at 95° C. for 5 min and slowly cooled down to room temperature over 30 min. 8 µL of different concentrations of MDPV were then mixed with 72 µL of the cDNA-Q:MA-F complex in the wells of a 384-well plate. After 10 min of incubation, fluorescence spectra were recorded from 655-850 nm with excitation at 648 nm at room temperature. The signal gain was calculated by $(F-F_0)/F_0$, where $F_0$ and F are the fluorescence intensity at 668 nm without and with MDPV, respectively.

Example 1—Binding Mechanism of Cy7 to TWJs

Cy7 (FIG. 1A) specifically binds to the TWJ-structured binding domain of a cocaine-binding aptamer via hydrophobic interactions.[19] Cocaine displaces Cy7 from the TWJ, resulting in a significant reduction in the absorbance of the dye at 760 nm. DIS- and DOG-binding aptamers both contain TWJ-structured target-binding domains. The generality of the Cy7-displacement assay was demonstrated using these two aptamers. Specifically, Cy7 was immediately displaced from both aptamers upon the addition of their respective targets, yielding a significant decrease in the absorbance of the dye at 760 nm (FIGS. 2A-2C).

To confirm that Cy7 indeed binds to TWJs in a sequence-independent manner, a 46-nt structured DNA pool containing a constant TWJ structure formed by three fully complementary stems (S1, S2, and S3) and 10 randomized nucleotides within the junction itself (FIG. 1A and Table 1, TWJ pool) was chemically synthesized. After mixing 2 µM Cy7 with 10 µM TWJ pool, an increase in the absorbance of the dye at 760 nm and 670 nm was observed, which respectively corresponds to binding of the Cy7 monomer and dimer to the TWJ pool (FIG. 1B).[11,12]

To assess the binding of the Cy7 to various domains within the TWJ pool, the isolated S1 stem was synthesized with an added terminal TTT loop (termed S1 stem-loop), the S2 stem-loop, and the S3 stem-loop (Table 1 and FIG. 3A) and the binding of Cy7 to each of them was characterized. None of these bound to the monomer (FIG. 3B), and the dimer only bound to the S1 stem-loop—most likely within its minor groove.[12] When Cy7 was incubated with a 1:1:1 mixture of the three isolated stem-loops, only binding of the dimer was observed (FIG. 1B). These results clearly indicated that the Cy7 monomer can only bind the aptamer within the fully-assembled TWJ domain.

The binding affinity of Cy7 monomer for the TWJ pool was obtained by titrating different concentrations of the pool into 2 μM Cy7. As the concentration of the TWJ pool increased, an increase in absorbance at 760 nm and a slight decrease in absorbance at 670 nm were observed (FIG. 4A). This provided further evidence that the TWJ domain preferentially binds to the Cy7 monomer. The decreased absorbance of the Cy7 dimer at higher DNA concentrations implies an equilibrium shift from dimer to monomer that favors Cy7 binding to the TWJ pool. Based on the absorbance at 760 nm, a $K_D$ of 6.4±0.8 μM was obtained (FIG. 4B). The binding stoichiometry of Cy7 monomer to the TWJ pool was further characterized using a Job plot.[13] The absorbance at 760 nm was measured at various Cy7:DNA ratios, with a constant total concentration of 5 μM. The maximum absorbance was observed at a mole fraction ($X_{Cy7}$) of 0.5, indicating that the TWJ pool binds to Cy7 in a 1:1 ratio. Since Cy7 monomer exclusively binds to the TWJ domain, each randomized TWJ in the pool should bind to a single Cy7 monomer (FIG. 1C).

These results show that the binding of Cy7 to TWJs is both structure-selective and sequence-independent, making it possible to isolate new small-molecule-binding aptamers with intrinsic dye-displacement functionality from a TWJ-structured SELEX library.

Example 2—Library Design and Isolation Process

A new small-molecule-specific aptamer isolated from a TWJ-containing library can be directly adopted into a label-free Cy7-displacement assay. A structured library was generated by extending both termini of the TWJ pool by 12 nt to create partial PCR primer binding sites (FIG. 5, Table 1, library). Changes in the sequence adjacent to the TWJ binding domain greatly affect the affinity of a cocaine-binding aptamer.[14,15] With this in mind, one base-pair in both stems 2 and 3 was randomized to further enhance the potential target-binding affinity of the aptamer. The resulting library is designed to primarily form TWJ-structured target-binding domains. Although there is small possibility to have non-TWJ-structured aptamers in the final enriched pool, these sequences can be identified and removed after sequencing. It should be noted that the randomness of this library ($4^{14}$ sequences) is considerably lower than many reported SELEX libraries.[8,16,17] However, this should not be of concern, as small-molecule targets can only interact with a limited number of nucleotides within an aptamer's binding domain. In fact, several small-molecule-binding aptamers have been isolated using a TWJ-structured library representing no more than $4^8$ sequences.[9]

This TWJ-structured library was used along with a previously reported library-immobilized SELEX strategy[9] to isolate aptamers for MDPV, an emerging drug of abuse in the synthetic cathinone family. SELEX in a low ionic strength buffer (10 mM Tris-HCl, 20 mM NaCl, 0.5 mM $MgCl_2$, pH 7.4) was performed, as an excessive amount of ions can induce non-specific hydrophobic interactions[18] between the target and the TWJ binding domain, which disfavors the isolation of highly target-specific aptamers. The library was immobilized onto streptavidin-coated agarose beads through hybridization to a biotinylated complementary DNA (cDNA) strand (Table 1, cDNA-bio) that disrupts the TWJ structure (FIG. 5, left). In the presence of MDPV, library molecules that recognized this target underwent a conformational change and refolded into a TWJ structure, thereby detaching themselves from the biotinylated cDNA (FIG. 5, right). These aptamers were collected, PCR amplified, and used for the next round of selection. To further improve aptamer specificity, counter-SELEX at various rounds was sequentially performed against three molecules that are structurally similar to MDPV: amphetamine, methamphetamine, and dopamine.

Figure 6A:
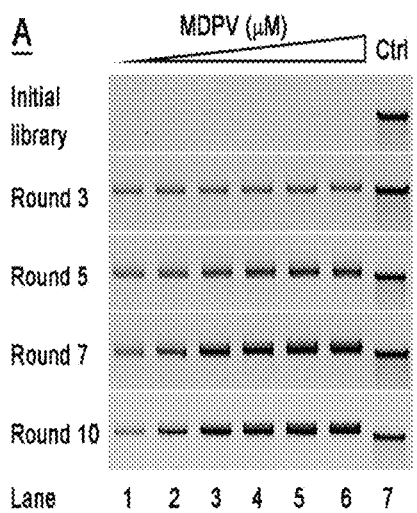
FIGS. 6A-6C show estimation of target affinity and specificity of the enriched pools during SELEX using a target elution assay. (6A) Target elution profile of the initial library and enriched pools after selection rounds 3, 5, 7, and 10 is analyzed by PAGE. Lanes 1-6 represent samples of the initial library and enriched pools eluted with 0, 10, 50, 100, 250, and 500 µM MDPV. Control samples (lane 7) containing 40 nM synthesized library are used to measure the concentration of eluted strands and percent elution of each sample. (6B) The MDPV binding affinity of the library and enriched pools are calculated based on the percent elution of each sample. (6C) The target specificity of the enriched pool after 10 rounds of SELEX is assessed by the target elution assay. Inset shows the enriched pool eluted with binding buffer (lane 1), 500 µM MDPV (lane 2), 500 µM methamphetamine (lane 3), 500 µM amphetamine (lane 4), and 500 µM dopamine (lane 5).
Figure 6B:
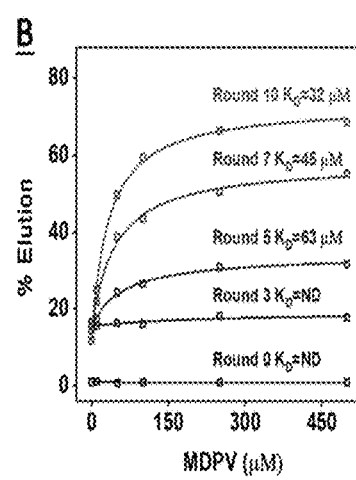
Figure 6C:
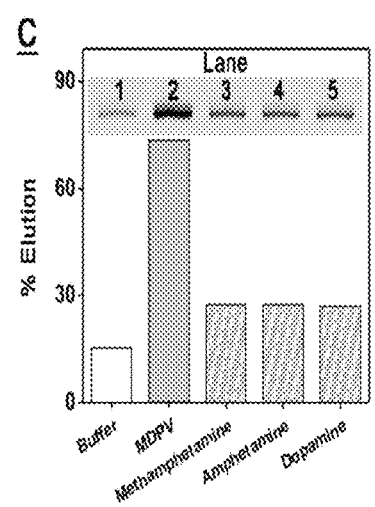
Figure 7:
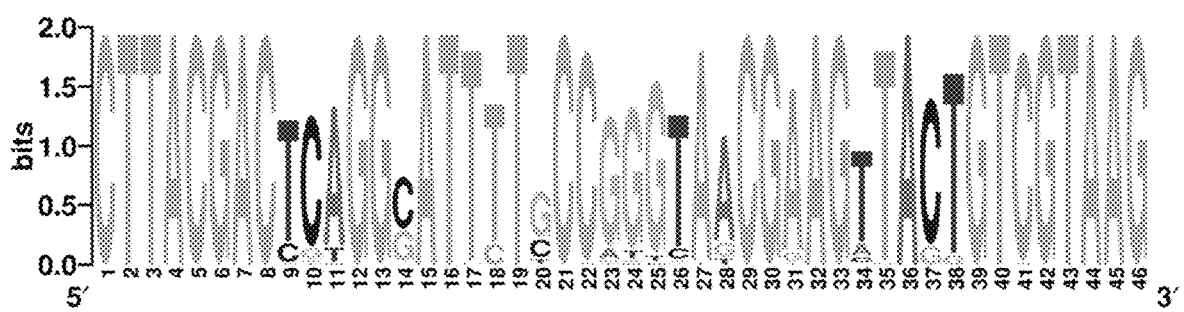
FIG. 7 shows sequence (SEQ ID NO: 17) logo for 50 clones isolated after 10 rounds of SELEX, showing the relative frequency of every nucleotide at each position. Nucleotides at pre-determined positions are marked grey, while the positions with randomized nucleotides are color-coded to show the distribution of different nucleotides. Higher frequency nucleotides appear in a larger font-size.

After each round of SELEX, the target affinity and specificity of the enriched pool was estimated with a target elution assay. After 10 rounds of selection, the enriched pool achieved saturated target affinity and low cross-reactivity to the counter-SELEX targets (FIGS. 6A-6C). The isolated aptamers were then cloned and sequenced. As expected, all sequences still retained the TWJ structure present in the original library. The 10 random nucleotides (FIG. 7, positions 9-11, 23-26, 36-38) in the TWJ binding domain exhibited a high level of consensus, with 41 out of 50 clones sharing an identical sequence at these sites. The four random nucleotide positions within the stems were more varied (FIG. 7, positions 14, 20, 28 and 34), but predominantly retained standard Watson-Crick base-pairing. The most highly-represented sequence was selected and the 12-nt partial primer-binding sites was truncated at both termini to generate the MDPV binding aptamer, termed MA (Table 1, MA).

Figure 8A:
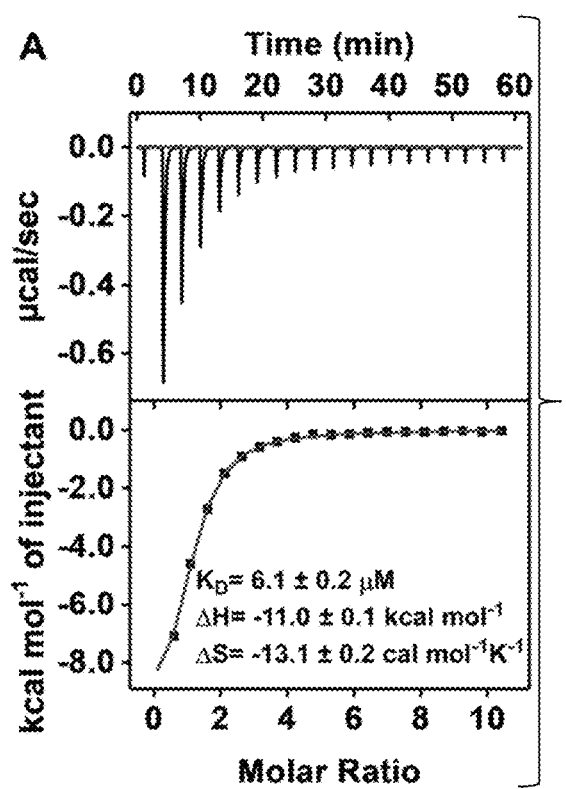
FIGS. 8A-8B show ITC characterization of MA binding to MDPV in the (8A) absence or (8B) presence of Cy7. The top panels display raw data, showing the heat generated from each titration of MDPV. The bottom panels show the integrated heat of each titration after correcting for dilution heat of the titrant.
Figure 8B:
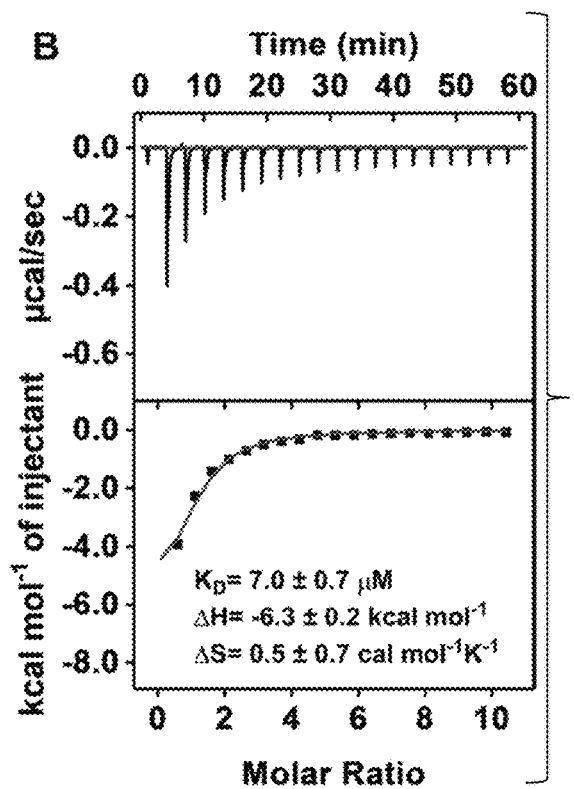

Example 3—Aptamer Characterization and Development of the Label-Free Cy7-Displacement Assay The binding affinity of MA was determined using isothermal titration calorimetry (ITC), titrating 1 mM MDPV into a 20 μM solution of the aptamer. It is shown that MA binds MDPV with a $K_D$ of 6.1±0.2 μM (FIG. 8A). Binding is driven by a negative enthalpy change (ΔH=−11.0±0.2 kcal/mol) but with a moderate entropy cost (ΔS=−3.9±0.2 kcal/mol) due to the fact that MDPV is constrained within the TWJ binding domain. It was anticipated that Cy7 would also hind to the TWJ domain of MA but could be displaced by MDPV. This was confirmed by performing an ITC experiment in which we titrated 1 mM MDPV into 20 μM Cy7-MA complex (1:1). The presence of Cy7 did not significantly reduce the MDPV affinity of MA ($K_D$=7.0±0.7 μM) (FIG. 8B). However, the binding heat (ΔH=−6.3±0.2 kcal/mol) was notably lower than in the absence of Cy7 (ΔH=−11.0±0.2 kcal/mol), indicating that a certain amount of energy was required for target-induced displacement of the dye.

Additionally, the higher binding entropy obtained with Cy7 (ΔS=0.6±0.7 kcal/mol) suggested positive entropy associated with the MDPV-mediated release of the dye from the aptamer. These results not only indicate that both Cy7 and MDPV can bind to the TWJ-structured binding domain, but also demonstrate that MDPV can efficiently displace Cy7.

MA could be directly adopted into a sensitive label-free colorimetric assay for the detection of MDPV, in which target-induced displacement of Cy7 from the aptamer TWJ binding domain produces a change in dye absorbance (FIG. 9A). Specifically, different concentrations of MDPV (0.1-640 μM) was added to a solution containing Cy7-MA complexes, and the absorption spectra was then immediately recorded. Within seconds, a progressive reduction of absorbance at 760 nm and enhancement of absorbance at 670 nm was observed (FIG. 9B). Using the absorbance ratio at 670/760 nm as an indicator, a linear range from 0-40 µM was obtained, with a low detection limit of 300 nM (FIG. 9C).

Notably, MA was highly cross-reactive to a variety of other synthetic cathinones (methylone, pentylone, naphyrone and mephedrone) that share the same beta-keto phenethylamine core structure as MDPV but with different side-chains (FIG. 10A). MA cross-reactivity to these four synthetic cathinones was tested at concentrations of 50 µM and 250 µM in the Cy7-displacement assay. Cross-reactivity greater than 65% and 80% for all four molecules was observed at concentrations of 50 µM (FIG. 10B) and 250 µM (FIG. 11), respectively. This suggests that MA specifically recognizes the core structure of synthetic cathinones rather than their side chain substituents.

Interestingly, naphyrone showed exceptionally high cross-reactivity compared to other synthetic cathinones, possibly due to the hydrophobicity of its naphthalene moiety. The high cross-reactivity of MA is desirable for onsite detection of the entire synthetic cathinone family, which is an important feature given that new derivatives of these drugs are continually being developed. In contrast, MA was not responsive to non-synthetic cathinone interfering agents. No specific signal was observed from any of our three counter-SELEX targets (FIG. 10C) in our Cy7-displacement assay at concentrations of 50 µM (FIG. 10B) or 250 µM (FIG. 11), despite their structural similarity to MDPV.

Figure 11:
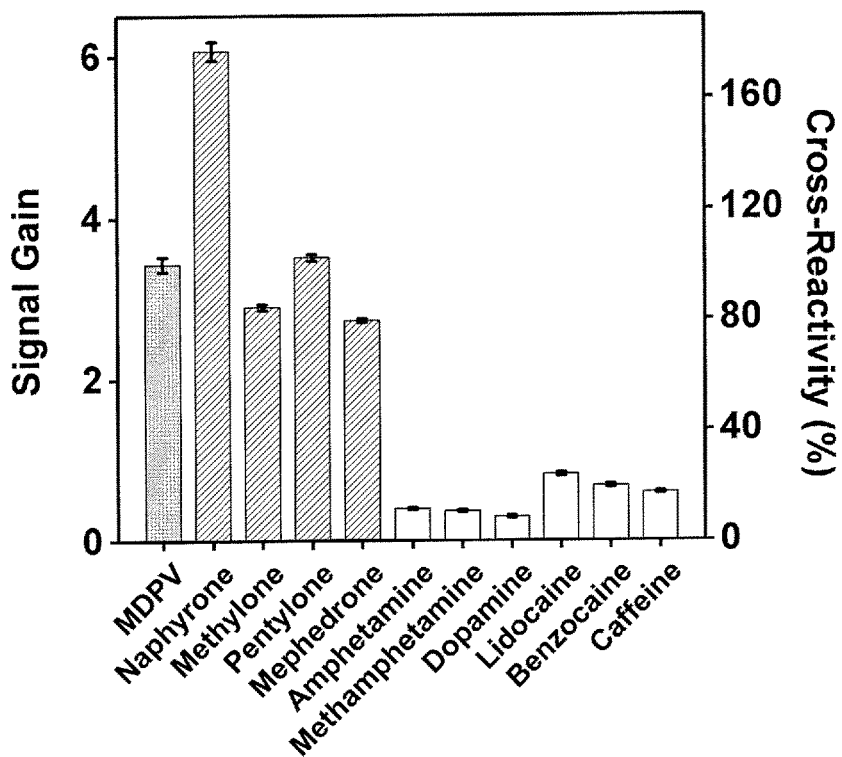
FIG. 11 shows cross-reactivity and specificity of our Cy7-displacement assay with 250 µM MDPV, other synthetic cathinones, or interfering agents (structurally-similar non-cathinone compounds and common cutting agents). Signal gain is calculated by $(R-R_0)/R_0$, where R and $R_0$ are the absorbance ratio at 670/760 nm with and without target or interfering agent, respectively. Error bars show standard deviation from three measurements of each compound tested.

The specificity of the assay was further tested against lidocaine, benzocaine, and caffeine, which are cutting agents commonly found in seized substances (FIG. 10C), and likewise observed little cross-reactivity at either concentration (FIGS. 10B and 11). It should be noted that the counter-SELEX targets and cutting agents either do not contain all the moieties present in MDPV (a phenyl ring, a ketone, and an amine group), or have all of these moieties but arranged in different positions. These results indicate that MA target recognition requires multiple specific interactions in a certain arrangement.

Example 4—Comparison of Cy7-Displacement and Strand-Displacement Assays

Figure 12:
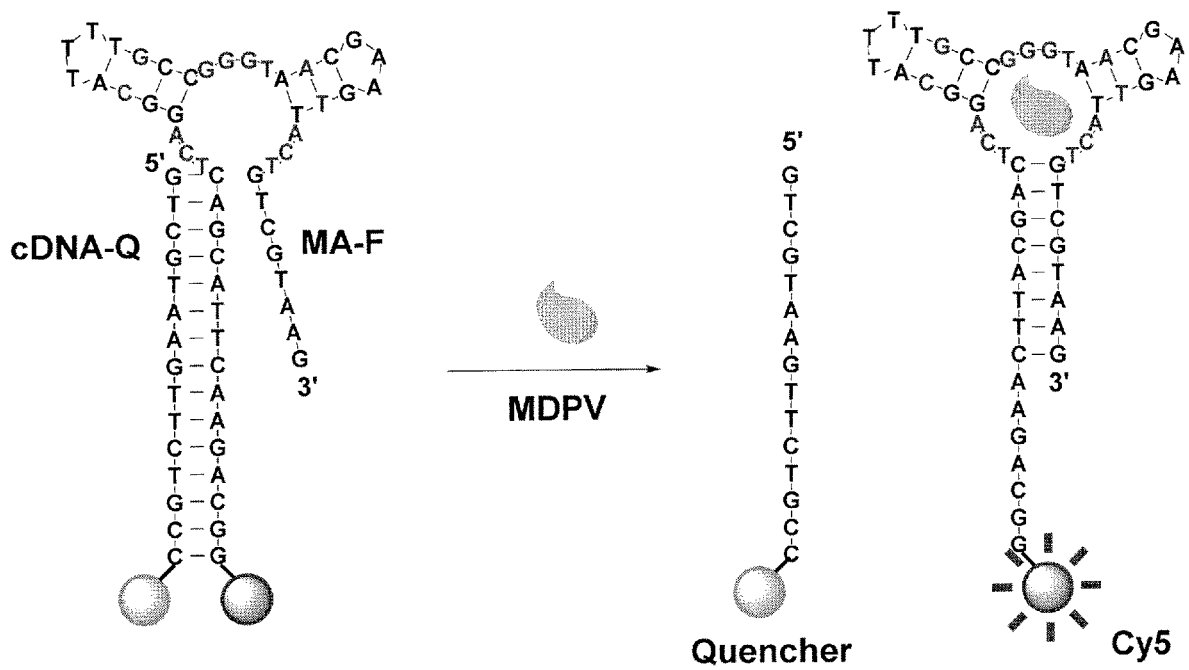
FIG. 12 shows the working principle of a conventional strand-displacement fluorescence assay. In the absence of MDPV (left), MA-F (SEQ ID NO: 14) forms a 15-bp duplex with cDNA-Q (SEQ ID NO: 16), which situates the fluorophore in close proximity to the quencher, thus quenching fluorescence. MDPV induces a target-induced conformational change in MA-F (right), forming a TWJ structure that results in dissociation of cDNA-Q, generating a measurable fluorescence signal.

The sensitivity of our Cy7-displacement colorimetric assay was compared with a strand-displacement fluorescence assay (FIG. 12) based on the same MDPV-binding aptamer. A fluorophore-modified version of MA (Table 1, MA-F) and a quencher-modified complementary strand (Table 1, cDNA-Q) was generated.

In the absence of MDPV, MA-F forms a 15-bp duplex with cDNA-Q that situates the fluorophore in close proximity to the quencher. The fluorescence of 50 nM MA-F was almost completely quenched in the presence of 50 nM cDNA-Q (FIG. 13A). Different concentrations of cDNA-Q was subsequently titrated into 50 nM MA-F and a $K_D$ of 0.5±0.2 nM (FIG. 13A, inset) was obtained. In the presence of MDPV, the target induced a conformational change in MA-F, forming a TWJ structure that resulted in dissociation of cDNA-Q, generating a measurable fluorescence signal.

Less than 50% fluorescence recovery was observed upon adding various concentrations of MDPV up to 640 µM (FIG. 13B). A linear range of 0-20 µM was obtained, with a detection limit of 2.5 µM (FIG. 13C), eight-fold poorer than the Cy7-displacement assay. This is primarily because cDNA-Q has a much higher affinity for the aptamer than Cy7, which makes target-induced displacement of the complementary strand less energetically favorable.

To further illustrate this point, unmodified versions of MA-F (Table 1, MA-L) and cDNA-Q (Table 1, cDNA) was synthesized and ITC experiments was performed in which 1 mM MDPV into 20 µM of MA-L was titrated either with or without 20 µM cDNA. It is shown that MA-L has an affinity for MDPV almost identical to that of MA (FIG. 14A, $K_D$=6.2 µM) in the absence of cDNA. However, in the presence of 20 µM cDNA, no MDPV binding was observed (FIG. 14B), confirming that MDPV could not efficiently displace the cDNA from the aptamer. As a control, 1 mM MDPV was titrated into 20 µM Cy7-MA-L (1:1), and it is shown that the presence of Cy7 does not attenuate the MDPV binding affinity of MA-L (FIG. 14C, $K_D$=7.0 µM). These results clearly demonstrate that the Cy7-displacement assay is more sensitive than the strand-displacement assay for the detection of small-molecule targets.

Example 5—MDPV Detection by Cy7-Displacement Assay in Biological Samples

Figure 15:
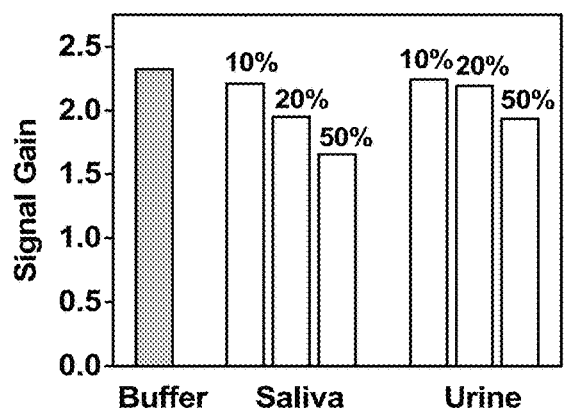
FIG. 15 shows signal gain measurements from the Cy7-displacement assay with 50 μM MDPV in buffer as well as different concentrations of saliva and urine (10%, 20%, and 50% saliva or urine prepared with buffer). Signal gain is calculated by $(R-R_0)/R_0$, where R and $R_0$ are the absorbance ratio at 670/760 nm with and without MDPV, respectively. Error bars show standard deviation from three measurements of each compound tested.
Figure 16A:
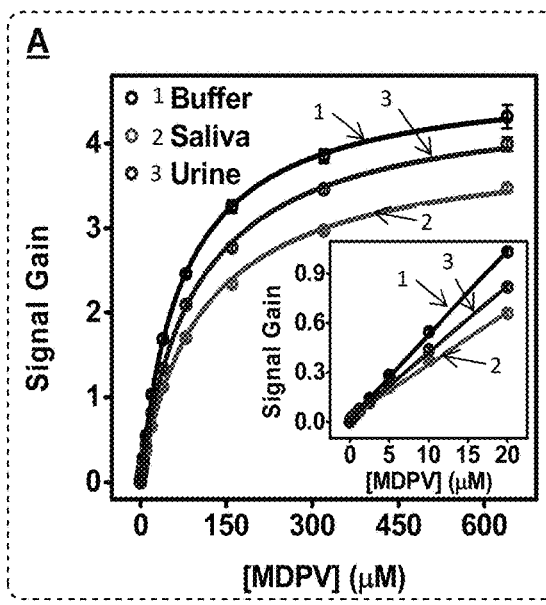
FIGS. 16A-16B show calibration curves for MDPV detection with Cy7-displacement assay in buffer, 50% saliva and 50% urine. (16A) Concentration-dependent response of signal gain to MDPV concentration. Inset shows assay performance at a linear range (0-20 μM). (16B) Linear relationship between signal gain and MDPV concentration within the range from 0 to 5 μM. Experimental conditions: [MA]=7 μM, [Cy7]=3 μM. Signal gain is calculated by $(R-R_0)/R_0$, where R and $R_0$ are the absorbance ratio at 670/760 nm with and without MDPV, respectively. Error bars represent the standard deviation of three measurements conducted at each MDPV concentration.
Figure 16B:
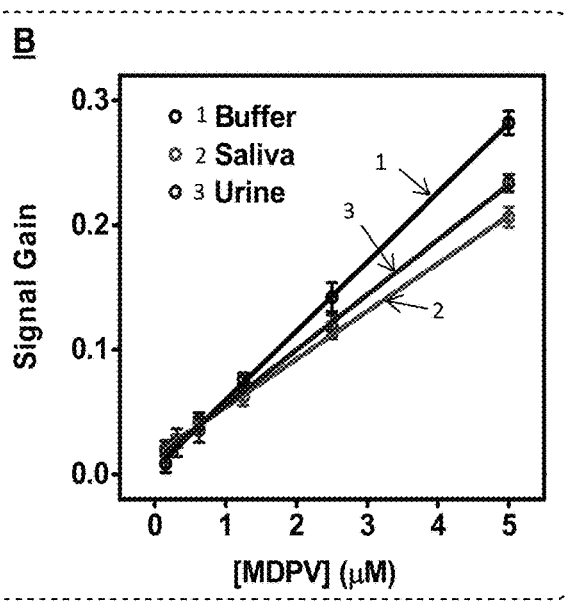

The Cy7-displacement assay was performed to detect MDPV in buffer, saliva, and urine. FIG. 15 shows signal gain measurements from the Cy7-displacement assay with 50 µM MDPV in buffer as well as different concentrations of saliva and urine (e.g., 10%, 20%, and 50%). It was also demonstrated that the signal gain from the Cy7-displacement assay is dependent on the concentration of MDPV (FIGS. 16A-16B). Specifically, the Cy7-displacement assay was performed in the presence of 3 µM Cy7 and 7 µM MA. The results showed that the assay had a linear range from 0 to 20 µM with a detection limit of 200 nM in buffer, saliva, and urine samples (FIG. 16A, inset and FIG. 16B). These results show that the Cy7-displacement assay can detect MDPV concentrations in biological samples, even in nanomolar ranges.

Thus, the Cy7-displacement assay can be used for biological samples of interest with unknown concentration of MDPV. By comparing the measured signal gain with the calibration curves (e.g., FIGS. 16A-16B), the MDPV concentration in the biological sample can be obtained.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES (1) Tuerk, C.; Gold, L. *Science* 1990, 249, 505-510.
(2) Song, S. P.; Wang, L. H.; Li, J.; Fan, C. H.; Zhao, J. L. *TrAC, Trends Anal. Chem.* 2008, 27, 108-117.
(3) Iliuk, A. B.; Hu, L. H.; Tao, W. A. *Anal. Chem.* 2011, 83, 4440-4452.
(4) Stojanovic, M. N.; de Prada, P.; Landry, D. W. *J. Am. Chem. Soc.* 2001, 123, 4928-4931.
(5) Stojanovic, M. N.; de Prada, P.; Landry, D. W. *J. Am. Chem. Soc.* 2000, 122, 11547-11548.
(6) Nutiu, R.; Li, Y. F. *J. Am. Chem. Soc.* 2003, 125, 4771-4778.
(7) Rajendran, M.; Ellington, A. D. *Nucleic Acids Res.* 2003, 31, 5700-5713.
(8) Nutiu, R.; Li, Y. F. *Angew. Chem., Int. Ed.* 2005, 44, 1061-1065.
(9) Yang, K.-A.; Pei, R. J.; Stefanovic, D.; Stojanovic, M. N. *J. Am. Chem. Soc.* 2012, 134, 1642-1647.
(10) Crooks, G. E.; Hon, G.; Chandonia, J. M.; Brenner, S. E. *Genome Res.* 2004, 14, 1188-1190.
(11) Choi, J. K.; D'Urso, A.; Trauernicht, M.; Shabbir-Hussain, M.; Holmes, A. E.; Balaz, M. *Int. J. Mol. Sci.* 2011, 12, 8052-8062.
(12) Garoff, R. A.; Litzinger, E. A.; Connor, R. E.; Fishman, I.; Armitage, B. A. *Langmuir* 2002, 18, 6330-6337.
(13) Seifert, J. L.; Connor, R. E.; Kushon, S. A.; Wang, M.; Armitage, B. A. *J. Am. Chem. Soc.* 1999, 121, 2987-2995.
(14) Roncancio, D.; Yu, II. X.; Xu, X. W.; Wu, S.; Liu, R.; Debord, J.; Lou, X. H.; Xiao, Y. *Anal. Chem.* 2014, 86, 11100-11106.
(15) Neves, M. A.; Reinstein, O.; Saad, M.; Johnson, P. E. *Biophys. Chem.* 2010, 153, 9-16.
(16) Oh, S. S.; Plakos, K.; Xiao, Y.; Eisenstein, M.; Soh, H. T. *ACS Nano* 2013, 7, 9675-9683.
(17) Yang, K.-A.; Barbu, M.; Halim, M.; Pallavi, P.; Kim, B.; Kolpashchikov, D. M.; Pecic, S.; Taylor, S.; Worgall, T. S.; Stojanovic, M. N. *Nat. Chem.* 2014, 6, 1003-1008.
(18) Zangi, R.; Hagen, M.; Berne, B. J. *J. Am. Chem. Soc.* 2007, 129, 4678-4686.
(19) Stojanovic, M. N.; Landry, D. W. *J. Am. Chem. Soc.* 2002, 124, 9678-9679

What is claimed is:

1. An aptamer-based sensor comprising an aptamer, the aptamer comprising SEQ ID NO: 12 and having a maximal length of 73 nucleotides.

2. The aptamer-based sensor according to claim 1, the aptamer being SEQ ID NO: 12.

3. The aptamer-based sensor according to claim 1, the aptamer having a maximal length of 53 nucleotides.

4. The aptamer-based sensor according to claim 1, the aptamer having a maximal length of 51 nucleotides.

5. The aptamer-based sensor according to claim 1, the aptamer comprising SEQ ID No: 13 and having a maximal length of 73 nucleotides.

6. The aptamer-based sensor according to claim 1, the aptamer comprising SEQ ID No: 14 and having a maximal length of 73 nucleotides.

7. The aptamer-based sensor according to claim 1, the aptamer being SEQ ID No: 13.

8. The aptamer-based sensor according to claim 1, the aptamer being SEQ ID No: 14.

9. The aptamer-based sensor according to claim 1, the aptamer binding to a dye.

10. The aptamer-based sensor according to claim 9, the dye being Cy7.

11. A method for detecting a synthetic cathinone in a sample comprising contacting the sample with the aptamer-based sensor according to claim 1, and detecting the synthetic cathinone in the sample, the detection comprising measuring a signal generated upon binding of the small-molecule target to the aptamer-based sensor, the signal being a change in absorbance or fluorescence intensity.

12. The method according to claim 11, wherein the sample is a biological sample or an environmental sample.

13. The method according to claim 12, wherein the biological sample is selected from blood, plasma, urine, tears, and saliva.

14. The method according to claim 11, wherein the synthetic cathinone being 3, 4-methylenedioxypyrovalerone (MDPV), naphyrone, methylone, pentylone, mephedrone, ethylone, butylone, pyrovalerone, 3-methylmethcathinone (3-MMC), or 3',4'-methylenedioxy-α-pyrrolidinopropiophenone (MDPPP).

15. The method according to claim 11, the aptamer-based sensor comprising a dye.

16. The method according to claim 15, the dye being Cy7.

17. The method according to claim 11, the synthetic cathinone having a core structure of:

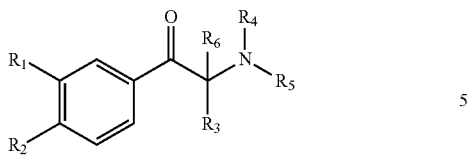

wherein $R_1$ and $R_2$, are each independently selected from the group consisting of hydrogen, alkyl, and alkoxy; or $R_1$ and $R_2$, taken together with the carbon atoms to which they are attached, form a substituted or unsubstituted 5- or 6-membered methylenedioxy group or aromatic ring;

$R_3$ is alkyl;

$R_4$ and $R_5$ are each independently selected from the group consisting of hydrogen and alkyl; or $R_4$ and $R_5$, taken together with the nitrogen atom to which they are attached, form a substituted or unsubstituted 5- or 6-membered pyrrolidino group; and $R_6$ is hydrogen.

18. The method according to claim 17, wherein $R_1$ and $R_2$ together form a methylenedioxy group or an aromatic ring, and $R_4$ and $R_5$ together form a pyrrolidino group.

* * * * *